(12) United States Patent
Tanabe et al.

(10) Patent No.: US 10,365,235 B2
(45) Date of Patent: Jul. 30, 2019

(54) RADIATION PHASE-CONTRAST IMAGING DEVICE

(71) Applicant: Shimadzu Corporation, Kyoto (JP)

(72) Inventors: Koichi Tanabe, Uji (JP); Shingo Furui, Nara (JP); Hiroyuki Kishihara, Kizugawa (JP); Kenji Kimura, Yamatokoriyama (JP); Taro Shirai, Kyoto (JP); Takahiro Doki, Kyotanabe (JP); Satoshi Sano, Uji (JP); Akira Horiba, Uji (JP)

(73) Assignee: Shimadzu Corporation, Nishinokyo-Kuwabaracho, Nakagyo-ku, Kyoto-shi, Kyoto (JP)

( * ) Notice: Subject to any disclaimer, the term of this patent is extended or adjusted under 35 U.S.C. 154(b) by 279 days.

(21) Appl. No.: 15/538,622

(22) PCT Filed: Nov. 20, 2015

(86) PCT No.: PCT/JP2015/082795
§ 371 (c)(1),
(2) Date: Jun. 21, 2017

(87) PCT Pub. No.: WO2016/104008
PCT Pub. Date: Jun. 30, 2016

(65) Prior Publication Data
US 2017/0343486 A1  Nov. 30, 2017

(30) Foreign Application Priority Data

Dec. 22, 2014 (JP) .................................. 2014-258713
Mar. 17, 2015 (JP) ............................... 2015-0536441

(51) Int. Cl.
*G03H 5/00* (2006.01)
*G01N 23/04* (2018.01)
(Continued)

(52) U.S. Cl.
CPC ........... *G01N 23/04* (2013.01); *A61B 6/4291* (2013.01); *A61B 6/4429* (2013.01);
(Continued)

(58) Field of Classification Search
CPC ........... G01N 23/04; G01N 2223/1016; G01N 2223/501; A61B 6/4291; A61B 6/4429;
(Continued)

(56) References Cited

U.S. PATENT DOCUMENTS 5,812,629 A * 9/1998 Clauser .................. A61B 6/032
378/37
8,908,825 B2 * 12/2014 Ohara .................... A61B 6/484
378/145

(Continued)

FOREIGN PATENT DOCUMENTS

JP    2011-146587        7/2011
JP    2011-146587 A      7/2011

(Continued)

OTHER PUBLICATIONS

Office Action dated Jan. 16, 2018 in corresponding foreign application JP2016-566042.

(Continued)

*Primary Examiner* — Kiho Kim
(74) *Attorney, Agent, or Firm* — Muir Patent Law, PLLC

(57) ABSTRACT

Provided is a radiation phase-contrast imaging device capable of assuredly detecting a self-image and precisely imaging the internal structure of an object. According to the configuration of the present invention, the longitudinal direction of a detection surface of a flat panel detector is inclined with respect to the extending direction of an absorber in a phase grating. This causes variations in the position (phase) of a projected stripe pattern of a self-image at different positions on the detection surface. This is there- (Continued)

fore expected to produce the same effects as those obtainable when a plurality of self-images are obtained by performing imaging a plurality of times in such a manner that the position of the projected self-images on the detection surface varies. This alone, however, results in a single self-image phase for a specific region of the object. Therefore, according to the present invention, it is configured such that imaging is performed while changing the relative position of the imaging system and the object.

10 Claims, 15 Drawing Sheets

(51) Int. Cl.
    *A61B 6/00* (2006.01)
    *G21K 1/06* (2006.01)
    *G21K 1/10* (2006.01)

(52) U.S. Cl.
    CPC ............ *A61B 6/4476* (2013.01); *A61B 6/484* (2013.01); *A61B 6/487* (2013.01); *A61B 6/5235* (2013.01); *G01N 2223/1016* (2013.01); *G01N 2223/501* (2013.01); *G21K 1/067* (2013.01); *G21K 1/10* (2013.01); *G21K 2207/005* (2013.01)

(58) Field of Classification Search
    CPC ....... A61B 6/4476; A61B 6/484; A61B 6/487; A61B 6/5235; G21K 1/067; G21K 1/10; G21K 2207/005
    See application file for complete search history.

(56) References Cited

U.S. PATENT DOCUMENTS

| | | | | |
|---|---|---|---|---|
| 9,719,947 | B2* | 8/2017 | Yun | G01N 23/20075 |
| 2010/0322380 | A1* | 12/2010 | Baeumer | G21K 1/06 |
| | | | | 378/62 |
| 2011/0174957 | A1 | 7/2011 | Okada | |
| 2012/0099702 | A1* | 4/2012 | Engel | A61B 6/00 |
| | | | | 378/62 |
| 2012/0128126 | A1* | 5/2012 | Ishii | A61B 6/4291 |
| | | | | 378/62 |
| 2012/0236988 | A1* | 9/2012 | Den | G01N 23/046 |
| | | | | 378/36 |
| 2012/0236992 | A1* | 9/2012 | Engel | A61B 6/00 |
| | | | | 378/62 |
| 2012/0243658 | A1* | 9/2012 | Geller | A61B 6/00 |
| | | | | 378/16 |
| 2012/0281217 | A1 | 11/2012 | Ouchi et al. | |
| 2013/0070895 | A1* | 3/2013 | Ouchi | G01N 23/04 |
| | | | | 378/62 |
| 2014/0126690 | A1* | 5/2014 | Yamaguchi | A61B 6/484 |
| | | | | 378/36 |
| 2015/0260663 | A1* | 9/2015 | Yun | G01N 23/20075 |
| | | | | 378/36 |
| 2015/0355112 | A1* | 12/2015 | Sato | A61B 6/484 |
| | | | | 708/205 |
| 2016/0172148 | A1* | 6/2016 | Behling | G21K 1/02 |
| | | | | 378/36 |
| 2016/0270198 | A1* | 9/2016 | Behling | G21K 1/02 |
| 2017/0156686 | A1* | 6/2017 | Koehler | A61B 6/06 |
| 2017/0303867 | A1* | 10/2017 | Roessl | A61B 6/025 |
| 2017/0343486 | A1* | 11/2017 | Tanabe | G01N 23/04 |

FOREIGN PATENT DOCUMENTS

| | | |
|---|---|---|
| JP | 2011-153969 | 8/2011 |
| JP | 2011-153969 A | 8/2011 |
| WO | WO 2009/104560 A1 | 8/2009 |

OTHER PUBLICATIONS

International Search Report dated Feb. 9, 2016 of PCT/JP2015/082795.

* cited by examiner

Self-image

Image obtained as self-image

Moving direction

Self-image

RADIATION PHASE-CONTRAST IMAGING DEVICE

TECHNICAL FIELD

The present invention relates to a radiation phase-contrast imaging device capable of imaging an internal structure of an object utilizing a phase-contrast of radiation transmitted through the object.

BACKGROUND TECHNIQUE

Conventionally, various devices have been conceived as a radiation imaging device for imaging an internal structure of an object by making radiation transmit through the object. A commonly-used radiation imaging device is configured to image a radiation projection image by irradiating radiation to an object to make the radiation transmit through the object. In such a projection image, shading appears depending on the ease of permeation of radiation, which represents the internal structure of the object.

With such a radiation imaging device, only objects having a property capable of absorbing radiation to some extent can be imaged. For example, soft biological tissues hardly absorb radiation. Even if it is tried to image such a tissue with a general device, nothing is reflected in the projection image. When trying to image the internal structure of an object that does not absorb radiation as described above, there is a theoretical limit in a general radiation imaging device.

Under the circumstances, a radiation phase-contrast imaging device that images an internal structure of an object utilizing a phase-contrast of transmitted radiation has been proposed. Such a device is configured to image an internal structure of an object using Talbot interference.

Talbot interference will be described. From the radiation source 53 shown in FIG. 26, phase-aligned radiation is irradiated. When making the radiation transmit through the phase grating 55 which is in a streak form, the image of the phase grating 55 appears on the projection surface which is apart from the phase grating 55 by a predetermined distance (Talbot distance). This image is called self-image. The self-image is not just a projection image of the phase grating 55. The self-image occurs only at the position where the projection surface is separated from the phase grating 55 by the Talbot distance. The self-image is configured by the interference fringes caused by interference of light. The reason that the self-image of the phase grating 55 appears at the Talbot distance is that the phase of radiation generated from the radiation source 53 is aligned. When the phase of radiation is disturbed, the self-image appearing at the Talbot distance is also disturbed.

The radiation phase-contrast imaging device is configured to image an internal structure of an object utilizing the self-image disturbance. It is assumed that an object is placed between the radiation source and the phase grating 55. Since this object hardly absorbs radiation, most of the radiation incident on the object exits to the phase grating 55 side.

The radiation has not passed through the object completely as it is. The phase of the radiation changes while passing through the object. The radiation exited the object passes through the phase grating 55 with the phase changed. The observation of the radiation on the projection plane arranged at the Talbot distance shows disturbances in the self-image of the phase grating 55. The degree of disturbances of the self-image represents the radiation phase change.

The specific magnitude of the phase change of the radiation that transmitted through the object changes depends on where the radiation has transmitted through the object. If the object has a homogeneous configuration, the change of the radiation phase remains the same no matter where the radiation transmits through the object. In general, however, an object has some internal structure. When making radiation transmit through such an object, the phase change does not remain the same.

Therefore, when the phase change is known, the internal structure of the object can be grasped. The phase change can be known by observing the self-image of the phase grating 55 at the Talbot distance.

In such an apparatus, how to observe the self-image becomes a problem. The self-image has the same streak pattern as the pattern of the phase grating 55. The streak pattern needs to be considerably finer to the extent that Talbot interference occurs. It is technically extremely difficult to image such a very fine pattern. This is because a detector equipped with extremely small detection elements is required for the self-image detection.

Therefore, in some conventional configurations, there are configurations that give up detecting the self-image itself with detectors. That is, in a conventional configuration, as shown in FIG. 27, another grating (absorption grating 57) is set on a detection surface of a detector. The absorption grating 57 has a streak structure similar to the phase grating 55. Therefore, the self-image incident on the absorption grating 57 interferes with the absorption grating 57 to generate a moire. This moire has a pattern in which dark lines are arranged, and since the pitch between the dark lines is large, imaging can be sufficiently performed even if the size of the detection element is large. By detecting this moire, the self-image can be obtained indirectly (see, for example, Patent Document 1).

PRIOR ART

Patent Document

[Patent Document 1] International Patent Laid-Open Publication No. 2009104560

SUMMARY OF THE INVENTION

Problems to be Solved by the Invention

However, the conventional radiation phase-contrast imaging device has the following problems. That is, also in the conventional radiation phase-contrast imaging device, it is difficult to manufacture it. Even with the configuration in which the absorption grating 57 is placed on the detection surface of the detector, it is difficult to realize a radiation phase-contrast imaging device.

In order to assuredly generate a moire, the absorption grating 57 is required to have a high absorption rate. The pitch of the phase grating 55 of the absorption grating 57 needs to be narrow enough to interfere with the self-image. It is extremely difficult to produce such absorption grating 57. In order to increase the absorption rate of the absorption grating 57, a certain thickness will be required for the absorption grating 57. When the absorption grating 57 becomes thicker, it becomes difficult to obtain the precision of the grating arrangement.

When the moire is observed with an absorption grating 57 with poor precision, the moire becomes distorted due to the disturbance of the absorption grating 57, which adversely affects the imaging of the internal structure of the object. Therefore, if there is a method of directly detecting the self-image without relying on the absorption grating 57, it is preferable. However, if the configuration not equipped with the absorption grating 57 is applied as described above, there is no choice but to configure to detect the self-image itself. Since there is a limit to miniaturize the detection element of the detector, it is difficult to directly detect the self-image in the first place. Under the circumstances, it is required to configure such that a self-image imaging method does not require the absorption grating 57 and the miniaturization of the detection element.

The present invention has been made in view of such circumstances, and its object is to provide a radiation phase-contrast imaging device capable of assuredly imaging a self-image to image an internal structure of an object in detail.

Means for Solving the Problems

The present invention has the following configurations to solve the above-mentioned problems.

That is, the radiation phase-contrast imaging device according to the present invention includes an imaging system; the imaging system being composed of a radiation source configured to irradiate radiation, a grating in which an absorber absorbing the radiation and extending in one direction is arranged in a direction perpendicular to the one direction, and a detection unit configured to detect a self-image of the grating generated by Talbot interference on a detection surface in which a detection element configured to detect the radiation is arranged in a matrix in a plane; and a position changing unit configured to change a relative position of the imaging system and an object such that a projection of the object moves linearly on the detection surface while keeping a positional relation of the radiation source, the grating, and the detection unit. (A) A longitudinal direction which is a direction along which the detection elements on the detection surface of the detection unit are arranged is inclined with respect to an extending direction of the absorber of the grating.

[Functions/Effects] According to the present invention, a radiation phase-contract imaging device capable of generating a clearer projection image by extracting more information on the inside of the object as compared with a conventional device without miniaturizing the detection element can be provided. That is, according to the configuration of the present invention, the longitudinal direction of the detection surface is inclined with respect to the extending direction of the absorber. By configuring the detection unit and the grating as described above, the self-image of the phase grating appearing as a stripe pattern is reflected with the self-image inclined obliquely with respect to the detection surface. This state means that the position (phase) at which the stripe pattern of the self-image is reflected differs depending on the position of the detection surface. Therefore, according to the present invention, it is considered that the same effects as those obtainable when a plurality of images different in reflecting position (phase) to which the self-image is reflected are obtained can be realized.

However, by this alone, the self-image phase for a specific region of the object M is fixed to one. Therefore, according to the configuration of the present invention, the imaging is performed while changing the relative position of the imaging system and the object M to perform the imaging of the self-image for different phases at the same place of the object M. By performing such imaging, it is possible to obtain the information on the inside of the object that cannot be obtained unless a phase grating in which the absorption lines are arranged at a high density and a detection unit in which the detection element is miniaturized are used without changing the configuration of the detection unit.

Further, in the aforementioned radiation phase-contrast imaging device, it is more preferable that a lateral direction which is a direction along which the detection element on the detection surface of the detection unit be arranged be inclined with respect to an arrangement direction of the absorbers of the grating.

[Functions/Effects] The aforementioned configuration is a more specific configuration of the present invention. When the lateral direction which is a direction along which a detection element on the detection surface of the detection unit is arranged is inclined with respect to the arrangement direction of the absorbers of the grating, the detection direction which is a direction along which the detection elements on the detection surface of the detection unit are arranged is assuredly inclined with respect to the extending direction of the absorber of the grating.

Further, in the aforementioned radiation phase-contrast imaging device, it is more preferable that the detection surface of the detection unit include a rectangular region configured such that an array in which a stripe-shaped self-image of one cycle is reflected and the detection element is arranged in one row in the longitudinal direction is arranged in a lateral direction.

[Function/Effects] The aforementioned configuration is a more specific configuration of the present invention. When the detection surface of the detection unit includes a rectangular region configured such that an array in which a stripe-shaped self-image of one cycle is reflected and the detection element is arranged in one row in the longitudinal direction is arranged in a lateral direction, the position (phase) at which the stripe pattern of the self-image is reflected can be assuredly changed depending on the position of the detection surface.

Further, in the aforementioned radiation phase-contrast imaging device, it is more preferable that it further includes a radiation source controller configured to make the radiation source irradiate the radiation every time a projection of the object moves by an amount corresponding to one detection element on the detection surface.

[Function/Effects] The aforementioned configuration is a more specific configuration of the present invention. By configuring such that the radiation source executes irradiation of radiation every time the position changing unit changes the relative position of the object with respect to the imaging system by an amount corresponding to one detection element, it is possible to more assuredly perform imaging of the self-image.

Further, in the aforementioned radiation phase-contrast imaging device, it is more preferable that the grating include a region in which an absorber absorbing the radiation and extending in one direction is arranged in a direction perpendicular to the one direction, and a region in which an absorber absorbing the radiation and extending in an intersecting direction intersecting with the one direction are arranged in a direction perpendicular to the intersecting direction, and both the regions are arranged in a direction along which the projection of the object moves on the detection surface.

[Functions/Effects] According to the aforementioned configuration, it is possible to image two patterns of self-images different in the extending direction of the dark line by merely performing scan imaging against the subject only once.

According to the aforementioned configuration, it is possible to obtain more information on the internal structure of the object and generate a transparent image of the object.

Further, it may be configured such that a radiation phase-contrast imaging device includes an imaging system; the imaging system is composed of a radiation source configured to irradiate radiation, a grating in which an absorber absorbing the radiation and extending in one direction is arranged in a direction perpendicular to the one direction, (S) a detection unit configured to detect a self-image of the grating generated by Talbot interference on a detection surface on which a detection element configured to detect the radiation is arranged in a matrix in a plane; and a position changing unit configured to change a relative position of the imaging system and an object such that a projection of the object moves linearly on the detection surface while keeping a positional relation of the radiation source, the grating, and the detection unit. (B) A longitudinal direction which is a direction along which the detection element on the detection surface of the detection unit is arranged coincides with an extending direction of the absorber of the grating and is inclined with respect to a moving direction of the projection of the object on the detection surface.

[Functions/Effects] The aforementioned configuration shows another embodiment of the present invention. Even with the aforementioned configuration, a radiation phase-contract imaging device capable of generating a clearer projection image by extracting more information on the inside of the object as compared with a conventional device without miniaturizing the detection element can be provided. That is, according to the aforementioned configuration, the longitudinal direction of the detection unit is inclined with respect to the moving direction of the object relative to the imaging system. So, when the detection unit is observed from the moving direction, it looks that the detection elements are arranged at a pitch narrower than the width of one detection element.

In addition to this point of view, the aforementioned configuration is configured to detect the radiation at a higher density by repeating the imaging while changing the relative position of the imaging system and the object. By performing such imaging, it is possible to obtain the information on the inside of the object that cannot be obtained unless a grating in which absorbers are arranged at a high density and a detection unit in which the detection element is miniaturized are used, without changing the configuration of the detection unit.

Further, in the aforementioned radiation phase-contrast imaging device, it is more preferable that a lateral direction which is a direction along which the detection elements on the detection surface of the detection unit are arranged do not perpendicularly intersect with the moving direction of the projection of the object on the detection surface.

[Function and Effects] In the aforementioned configuration is a more specific configuration of the present invention, when the lateral direction which is an arrangement direction that the detection elements on the detection surface of the detection unit are arranged does not perpendicularly intersect with the moving direction of the object with respect to the imaging system, the longitudinal direction of the detection surface is inclined with respect to the moving direction of the object relative to the imaging system.

Further, in the aforementioned radiation phase-contrast imaging device, it is more preferable that on the detection surface of the detection unit, an oblique direction along which it advances by an amount corresponding to one detection element in a lateral direction as it advances from a given detection element in the longitudinal direction by an amount corresponding to three detection elements coincide with the moving direction of the projection of the object on the detection surface.

[Function/Effects] The aforementioned configuration is a more specific configuration of the present invention. Provided that the moving direction of the object with respect to the imaging system coincides with the oblique direction in which it advances in the lateral direction by an amount corresponding to one detection element as it advances in the detection direction by an amount corresponding to three detection elements on the detection surface, when the detection unit is observed from the moving direction, it looks that the detection elements are arranged at equal intervals, so it is possible to obtain a self-image more assuredly.

Further, in the aforementioned radiation phase-contrast imaging device, it is more preferable that it further include a radiation source controller configured to make the radiation source execute irradiation of the radiation every time the projection of the object on the detection surface moves by $1/10^{1/2}$ times a width of one detection element.

[Function/Effects] The aforementioned configuration is a more specific configuration of the present invention. By configuring such that the radiation source executes irradiation of radiation every time the position changing unit changes the relative position of the object with respect to the imaging system by $1/10^{1/2}$ times a width of one detection element, it is possible to more assuredly perform the imaging of the self-image.

Further, the following configuration exerts the same effects as those obtainable by the aforementioned radiation phase-contrast imaging device.

That is, it may be configured such that a radiation phase-contrast imaging device includes: an imaging system; the imaging system is composed of a radiation source configured to irradiate radiation, a grating in which an absorber absorbing the radiation and extending in one direction is arranged in a direction perpendicular to the one direction, and (S1) a detection unit configured to detect a self-image of the grating generated by Talbot interference on a detection surface for detecting the radiation; and a position changing unit configured to change a relative position of the imaging system and an object such that a projection of the object moves linearly on the detection surface while keeping a positional relation of the radiation source, the grating, and the detection unit. (C) An array configured by detection elements arranged in a inclined direction which is a direction inclined with respect to a longitudinal direction is two-dimensionally arranged by being arranged in a lateral direction perpendicular to the longitudinal direction on the detection surface of the detection unit. (A0) The inclined direction is inclined with respect to an extending direction of the absorber of the grating.

[Functions/Effects] Also with the aforementioned configuration, since the arrangement direction of the detection elements is inclined with respect to the extending direction of the absorber, the same effects as those obtainable by the aforementioned configuration can be obtained.

Effects of the Invention

According to the present invention, a radiation phase-contract imaging device capable of generating a clearer projection image by extracting more information on an inside of an object as compared with a conventional device without miniaturizing a detection element can be provided. That is, according to the configuration of the present invention, the longitudinal direction of the detection surface is inclined with respect to the extending direction of the absorber. So, the position (phase) at which the stripe pattern of the self-image is reflected assuredly differs depending on the position of the detection surface. Therefore, it is considered that the same effects as those obtainable when a plurality of self-images are obtained by performing plural imaging in which the self-images on the detection surface are different in reflecting position can be realized. However, by this alone, the self-image phase for a specific position of the object M is fixed to one. Therefore, according to the configuration of the present invention, the imaging is performed while changing the relative position of the imaging system and the object.

EMBODIMENT FOR CARRYING OUT THE INVENTION

Next, embodiments for carrying out the invention will be described with reference to each Example. The X-ray in Examples corresponds to the "radiation" of the present invention. The FPD in Examples is an abbreviation for a flat panel detector. The radiation phase-contrast imaging device of the present invention can image even an object M with less radiation absorption, and therefore it is suitable for a fluoroscopy of a substrate for industrial applications and a fluoroscopy of a breast, etc., for medical applications.

Example 1

Figure 1:
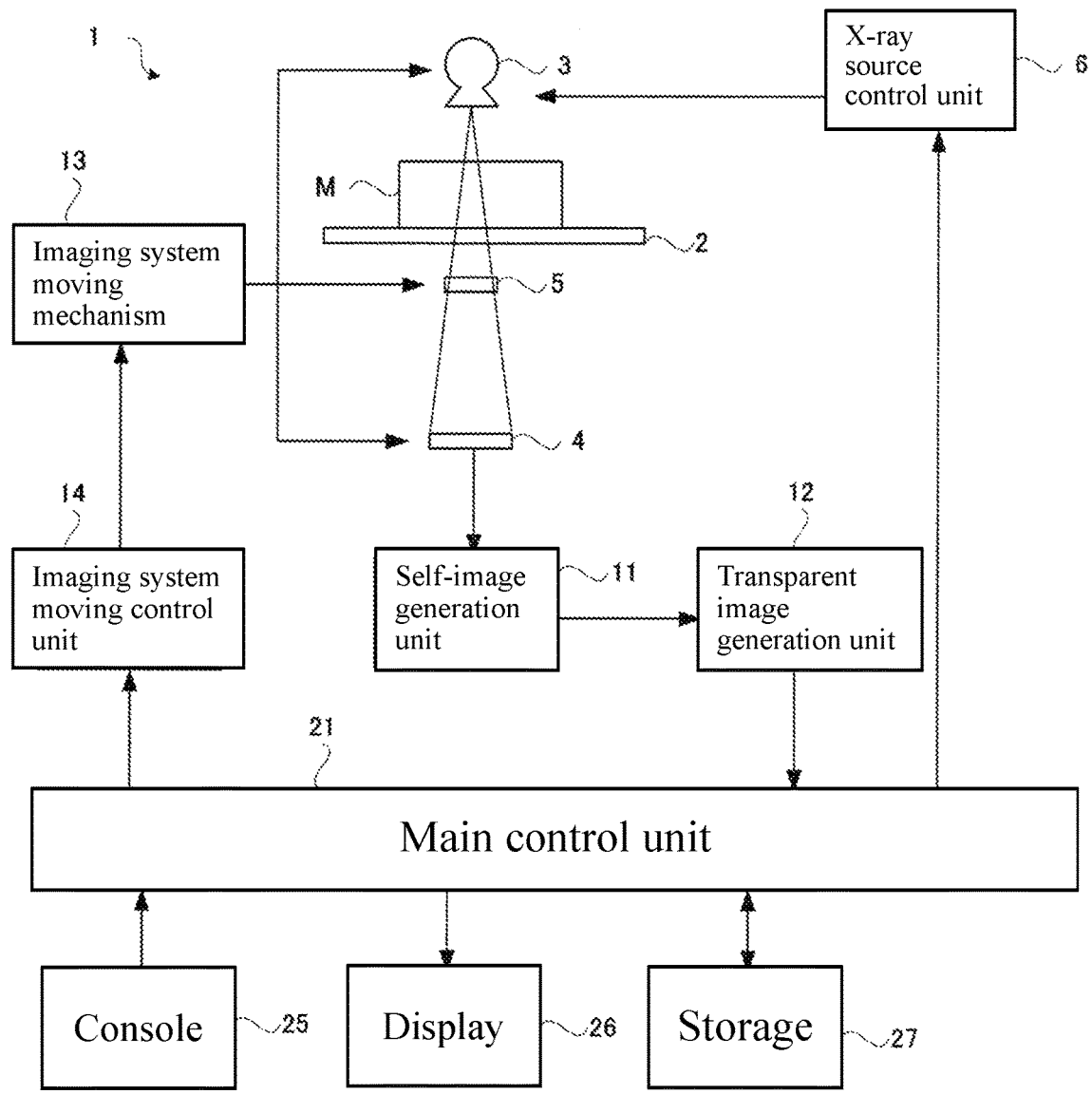
FIG. 1 is a functional block diagram illustrating the overall configuration of a radiation phase-contrast imaging device according to Example 1.

A radiation phase-contrast imaging device according to the present invention will be described. FIG. 1 shows the overall configuration of an imaging device 1 according to the present invention. As shown in FIG. 1, the imaging device 1 includes a platform 2 on which an object M is placed, an X-ray source 3 provided above the platform 2 and configured to irradiate an X-ray beam spreading in a pyramidal shape, and an FPD 4 for detecting the X-ray generated from the X-ray source 3 and transmitted through the object M on the platform 2. A phase grating 5 for generating Talbot interference is provided at a position between the FPD 4 and the platform 2. The X-ray source 3 corresponds to the "radiation source" of the present invention, and the FPD 4 corresponds to the "detection unit" of the present invention. The phase grating 5 corresponds to the "grating" of the present invention.

The imaging device 1 is a radiation imaging device utilizing Talbot interference. Therefore, the X-ray source 3 is configured to output a phase-aligned X-ray beam. The distance between the phase grating 5 and the FPD 4 is set to the Talbot distance. With this setting, the self-image of the phase grating 5 will appear on the detection surface of the FPD 4 that detects the X-ray.

The self-image generation unit 11 generates the self-image of the phase grating 5 based on the output of the FPD 4. The generated self-image is output to the transparent image generation unit 12. The transparent image generation unit 12 generates a transparent image in which the phase-contrast of the X-ray generated in the object M is imaged based on the self-image of the phase grating 5.

Figure 2:
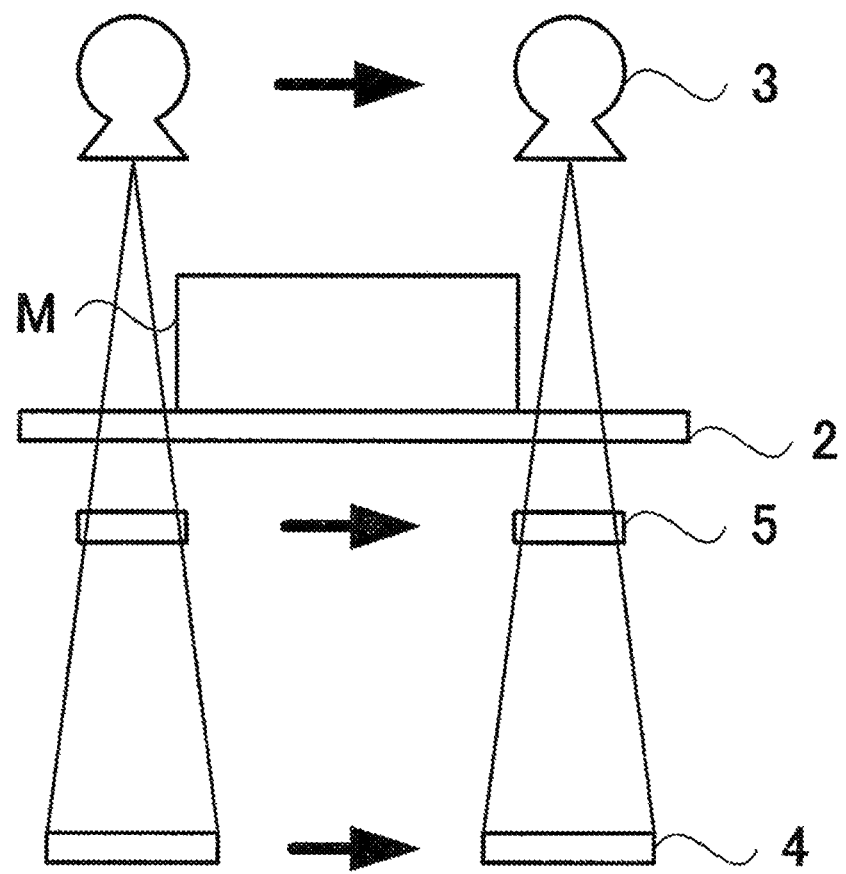
FIG. 2 is a schematic view illustrating the movement of the imaging system according to Example 1.

The imaging system moving mechanism 13 is configured to move the X-ray source 3, the FPD 4, and the phase grating 5 with respect to the platform 2 while maintaining the mutual positional relationship as shown in FIG. 2. With the imaging system moving mechanism 13, the X-ray source 3, the FPD 4, the phase grating 5 can move in a direction parallel to the platform 2. The imaging system moving mechanism 13 changes the relative position of the imaging system 3, 4, and 5 and the object M so that the projection of the object M linearly moves on the detection surface of the FPD 4 with the positional relationship among the X-ray source 3, the phase grating 5, and the FPD 4 maintained. The imaging system 3, 4, and 5 is composed of the X-ray source 3 which irradiates an X-ray, the phase grating 5 in which an absorption line 5a extending in one direction and absorbing the radiation is arranged in a direction perpendicular to the one direction, and the FPD 4 that detects the self-image of the phase grating 5 generated by the Talbot interference on the detection surface in which detection elements 4a detecting radiation are arranged in a matrix in a plane. Note that the absorption line 5a corresponds to the "absorber" of the present invention, and the imaging system moving mechanism 13 corresponds to the "position changing unit" of the present invention.

In the case of Example 1, the change of the relative position of the object M with respect to the imaging system 3, 4, and 5 can be performed by moving the imaging system 3, 4, and 5 without moving the object M. The imaging system moving control unit 14 is provided for the purpose of controlling the imaging system moving mechanism 13.

The imaging system moving control unit 14 is provided for the purpose of controlling the imaging system moving mechanism 13. During the imaging, the X-ray source control unit 6 controls the X-ray source 3 so as to repeatedly output an X-ray beam in a pulsed manner. Every time the X-ray source 3 outputs an X-ray beam, the FPD 4 detects the X-ray that transmitted through the object M on the platform 2 and the phase grating 5 and transfers the detection data to the self-image generation unit 11. In this way, the device of the present invention is configured to generate a self-image by continuously performing the X-ray imaging. The X-ray source control unit 6 corresponds to the "radiation source controller" of the present invention.

The continuous X-ray imaging is realized by the cooperation of the X-ray source control unit 6 and the imaging system moving control unit 14. That is, by the cooperation of them, the operation of moving the imaging system 3, 4, and 5 by the movement amount corresponding to the width of one pixel of the detection element on the FPD 4 and the operation of irradiating the X-ray beam are repeated. Therefore, as the continuous imaging is continued, the projected position of the object M on the FPD 4 moves one by one pixel. As described above, the X-ray source control unit 6 according to Example 1 makes the X-ray source 3 irradiate the radiation every time the imaging system moving mechanism 13 moves the projection of the object M by an amount corresponding to one detection element on the detection surface.

Figure 3:
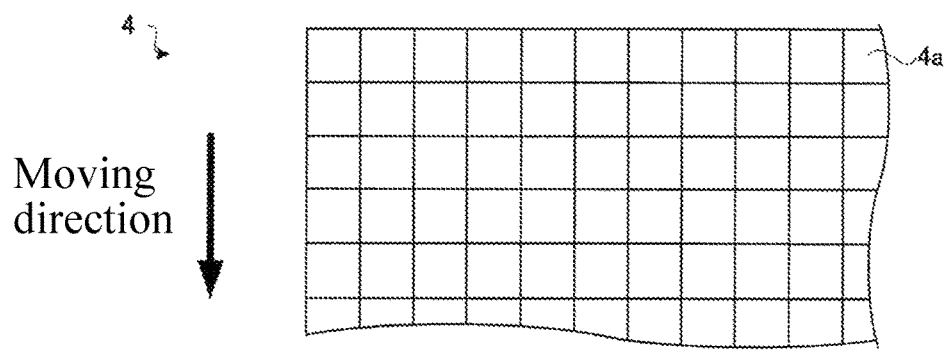
FIG. 3 is a plan view illustrating the configuration of an FPD according to Example 1.

FIG. 3 illustrates the detection surface of the FPD 4. On the detection surface of the FPD 4, detection elements 4a each having a rectangular shape of 20 μm in length×20 μm in width are arranged in a matrix in a plane. The longitudinal direction of the detection element 4a coincides with the moving direction of the imaging system 3, 4, and 5 realized by the imaging system moving mechanism 13. The detection surface of the FPD 4 has a rectangular shape with the moving direction of the imaging system 3, 4, and 5 as the longitudinal direction and the direction perpendicular to the moving direction as the lateral direction. The detection surface has a width of 20 cm in the longitudinal direction and a width of 2 cm in the lateral direction. The size of the detection element and that of the detection surface can be changed arbitrarily.

The FPD 4 is a direct conversion type X-ray detector. That is, the FPD 4 has a conversion layer for converting an X-ray into a pair of electron and hole (carrier pair). The carriers generated in the conversion layer are captured by and accumulated in each of the detection elements 4a. When a signal for outputting a carrier is sent to the detection element 4a, the detection element 4a outputs the accumulated carrier as a detection signal. The fineness of this detection element 4a is a main factor determining the spatial resolution of the FPD 4. The smaller the detection element 4a, the better the spatial resolution of the FPD 4, so that it is possible to detect a finer structure.

Figure 4:
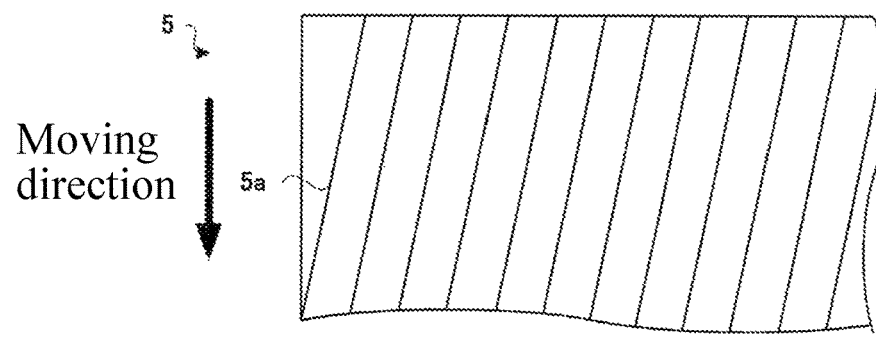
FIG. 4 is a plan view illustrating the configuration of the phase grating according to Example 1.

FIG. 4 illustrates the phase grating 5. The phase grating 5 has such a shape that the projection of the X-ray beam is reflected on the entire region of the detection surface of the FPD 4. Therefore, in the same manner as in the detection surface of the FPD 4, the phase grating 5 has a rectangular shape with the moving direction of the imaging system 3, 4, and 5 as the longitudinal direction and a direction perpendicular to the moving direction as the lateral direction.

The phase grating 5 has a plurality of absorption lines 5a absorbing an X-ray and extending linearly. The absorption line 5a is arranged at a predetermined pitch in a direction perpendicular to the extending direction thereof. The absorption line 5a is not extended in the moving direction of the imaging system 3, 4, and 5, but is inclined with respect to the moving direction. As described above, the longitudinal direction which is the arrangement direction of the detection elements 4a on the detection surface of the FPD 4 is inclined with respect to the extending direction of the absorption line 5a of the phase grating 5. In other words, the lateral direction which is the arrangement direction of the detection elements 4a on the detection surface of the FPD 4 is inclined with respect to the arrangement direction of the absorption lines 5a of the phase grating 5.

Figure 5:
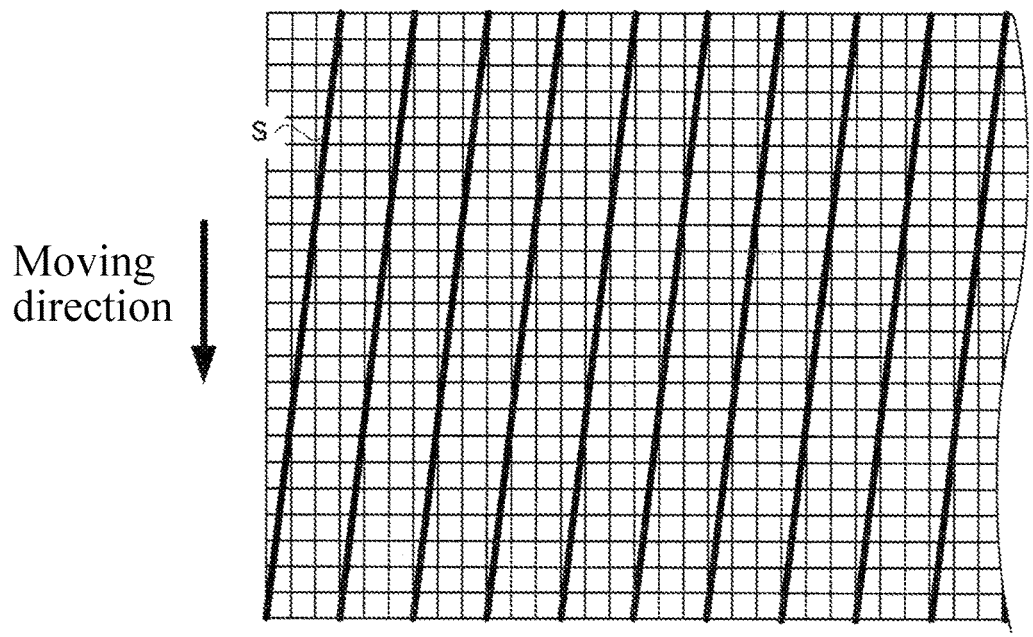
FIG. 5 is a plan view illustrating the configuration of the FPD according to Example 1.

FIG. 5 illustrates the state in which the projection of the phase grating 5 is reflected on the detection surface of the FPD 4. On the FPD 4, a plurality of dark lines S are reflected as a stripe pattern. This dark line S is not the projection itself of the absorption line 5a of the phase grating 5, but is the self-image of the phase grating 5 resulting from the Talbot interference. The self-image at this time is, intuitively speaking, formed by overlapping the interference fringes caused by the light interference.

According to FIG. 5, it can be seen that the dark line S on the FPD 4 extends obliquely with respect to the arrangement of the detection elements 4a. The reason that the extending direction of the dark line S is directed as described above is that the absorption line 5a of the phase grating 5 is inclined with respect to the longitudinal direction of the FPD 4. Since the extending direction of the dark line S coincides with the extending direction of the absorption line 5a of the phase grating 5, the dark line S on the FPD 4 is obliquely reflected on the FPD 4.

Further, according to FIG. 5, the pitch when the dark line S is arranged in the lateral direction corresponds to three detection elements. This pitch can be arbitrarily changed. Hereinafter, the following description will be made assuming that the dark line S is arranged in the lateral direction at a pitch of three pixels.

Figure 6:
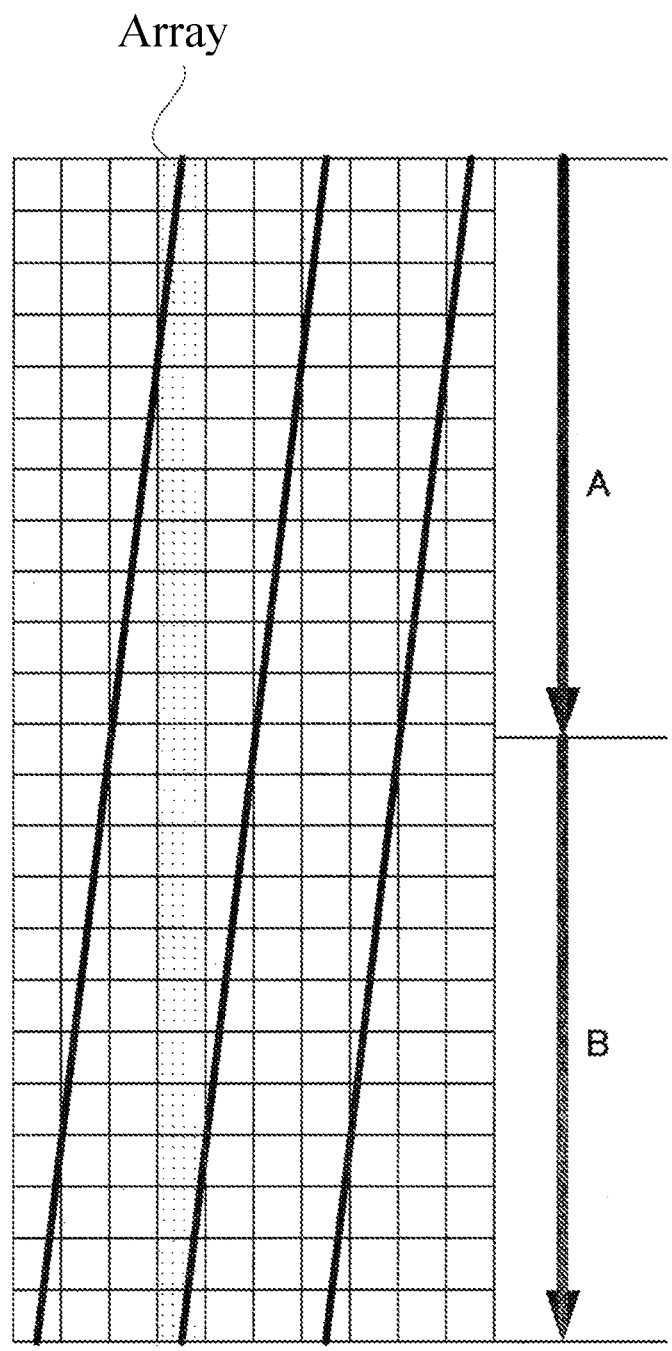
FIG. 6 is a plan view illustrating the configuration of the FPD according to Example 1.

FIG. 6 shows the relationship between the dark line S and the arrangement of the detection elements 4a in more detail. Attention is paid to the array in which the detection elements indicated by shading are arranged vertically in one line in FIG. 6. When observing this array from the top to the bottom, the followings can be found. That is, in the upper end portion of the array in FIG. 6, the dark line S is reflected. When observing the lower section of the array from there, the dark line S reflected in the array escapes toward the left side. When continuously observing the further lower section of the array, the array comes to a position sandwiched between adjacent dark lines S. At this time, the distance between the dark line S on the left side and the array and the distance between the dark line S on the right side and the array becomes equal. When further observing the lower section of the array, the dark line S which was on the right side of the array gradually approaches the array, and the dark line S is reflected at the lower end section of the array.

In other words, when observing the array from the top to the bottom, in the first half section indicated by the arrow A on the right side of FIG. 6, the dark line S which was superimposed on the array moves away from the array, and in the latter half section indicated by the arrow B, the dark line S which was separated from the array is superimposed on the array. In other words, in the array, all of the state in which the dark line S is completely superimposed on the array, the state in which the dark line S is not at all superimposed on the array, and the state in which the intermediate state therebetween are realized. That is, the detection surface of the FPD 4 has an array in which one cycle of the stripe-shaped self-image is reflected and the detection elements 4a are arranged in one row in the longitudinal direction.

The aforementioned phenomenon occurs not only in the array shown by the shading in FIG. 6 but also in all conceivable arrays on the FPD 4 in which the detection elements 4a are arranged vertically in one line. In other words, the detection surface of the FPD 4 is a rectangular region configured by arranging the aforementioned arrays in which one cycle of the self-image is reflected in the lateral direction. It may be configured such that the detection surface of the FPD 4 in Example 1 is extended so as to be longer than the aforementioned region so that the detection surface of the FPD 4 can reflect more than one cycle of the self-image.

<The Reason That the Spatial Resolution is Improved Due to the Inclination of the Absorption Line 5a>

Since the absorption line 5a of the phase grating 5 is inclined with respect to the moving direction of the imaging system 3, 4, and 5 and the arrangement of the detection elements like in the present invention, a transparent image high in spatial resolution can be obtained. This will be explained as follows.

Figure 7:
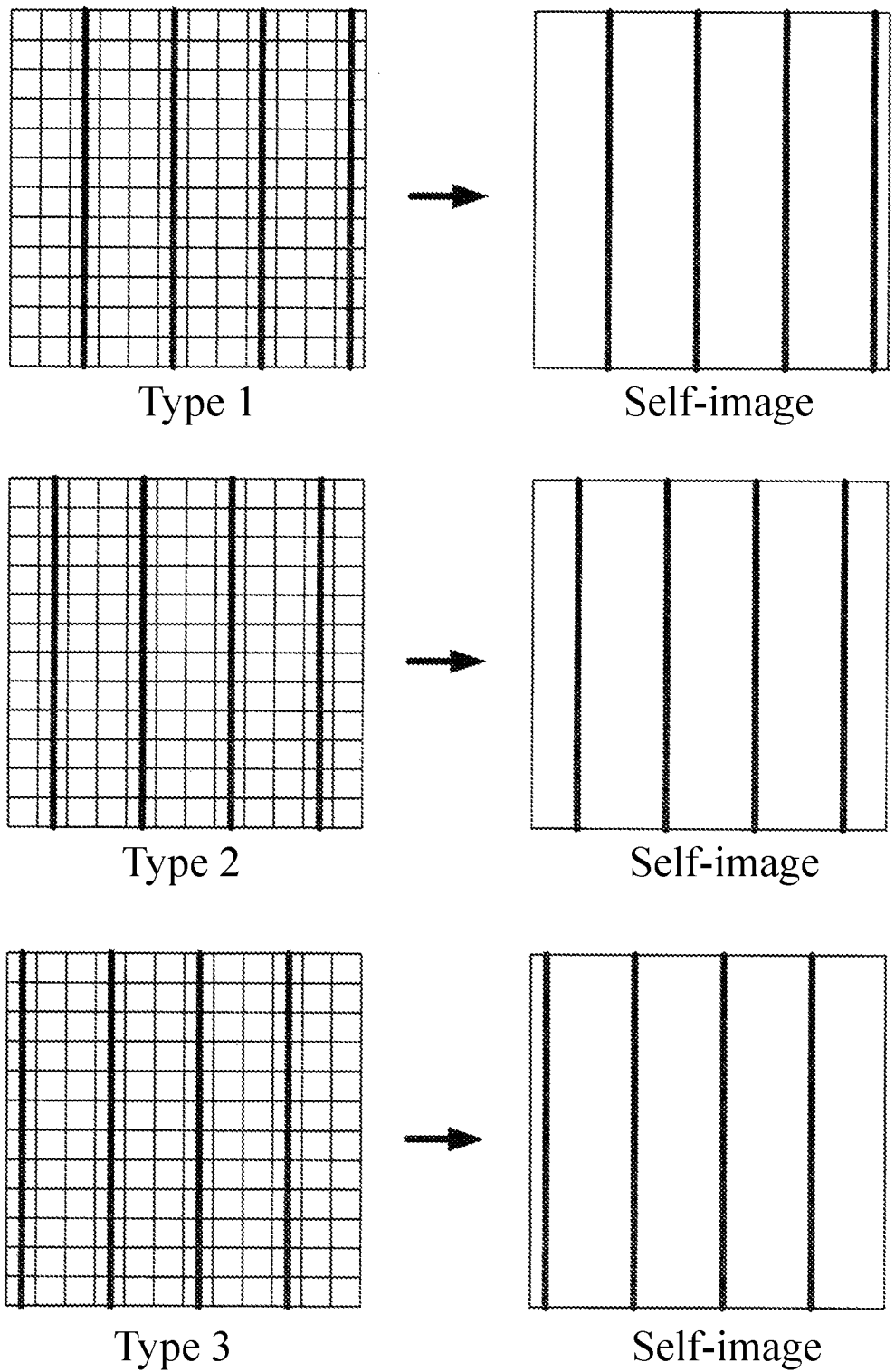
FIG. 7 is a schematic view illustrating the effects of the configuration of Example 1.

FIG. 7 shows a conventional radiation phase-contrast imaging device. In the conventional radiation phase-contrast imaging device, a movement of the imaging system 3, 4, and 5 with respect to the object M is not performed. As shown in the upper left side in FIG. 7, the dark line appearing on the detection surface of the FPD 4 extends along the arrangement of the detection elements. Each dark line is arranged at intervals wider than the width of one detection element. In FIG. 7, it is assumed that the interval between the adjacent dark lines is three times the width of the detection element.

As for how the dark line appears on the detection surface, three types are conceivable depending on the positional relationship of the phase grating 5 with respect to the FPD 4. The three types include: Type 1 in which the dark line appears on the third column, the sixth column, the ninth column, . . . , of the detection element arrays, which are columns of multiples of 3, as shown on the left side of the upper row in FIG. 7; Type 2 in which the dark line appears on the second row, the fifth row, the eighth column, . . . , of the detection element arrays, which are columns of the number obtained by subtracting 1 from multiples of 3, as shown on the left side of the middle row in FIG. 7; and Type 3 in which the dark line appears in the first row, the fourth row, the seventh column, . . . , of the detection element arrays, which are columns of the number obtained by subtracting 2 from triples of 3, as shown on the left side of the middle row of FIG. 7.

As shown on the right side in FIG. 7, the obtained self-images differ depending on the dark line appearance Types 1, 2, and 3 on the detection surface. That is, the position where the dark lines appears in the self-image differs depending on the Type.

That the dark line is inclined with respect to the FPD 4 like in the present present means that the appearance of the dark line differs in the FPD 4. In the case shown on the left side of the upper row in FIG. 7, the column on which the dark line is to be appeared is fixed. This is because the dark line and the detection element column are arranged in parallel. This situation is also applied to the cases shown in the middle row and the bottom row in FIG. 7. However, when the dark line is inclined with respect to the FPD 4, the detection element column on which the dark line is to be appeared differs depending on the location of the FPD 4. That is, the type of appearance of the dark line on the FPD 4 is Type 1 in a certain place, Type 2 in another place, and Type 3 in still another place. The type of actual appearance of the dark line on the FPD 4 according to the present invention includes an intermediate type in addition to Types 1, 2, and 3.

Figure 8:
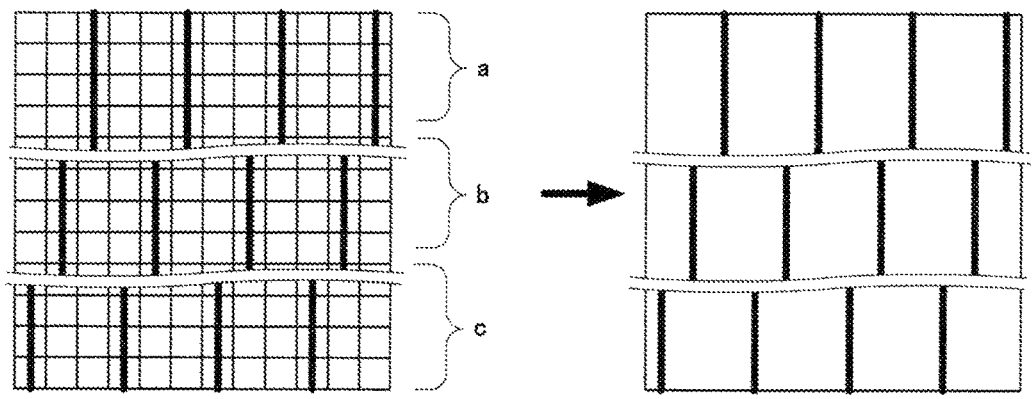
FIG. 8 is a schematic view illustrating the effects of the configuration of Example 1.

However, in order to briefly explain the effects of the present invention, the detection surface as shown on the left side in FIG. 8 will be considered. In the upper stage "a" of this detection surface, the appearance of the dark line is Type 1, and in the middle stage "b" of this detection surface, the appearance of the dark line is Type 2. In the lower stage "c" of the detection surface, the appearance of the dark line is Type 3. It is assumed that the upper stage, the middle stage, and the lower stage are arranged in the moving direction of the imaging system 3, 4, and 5.

The self-image obtained by the detection surface as shown on the left side in FIG. 8 differs in the dark line appearance position depending on the position of the image as shown on the right side in FIG. 8. This is because that how the dark line appears on the detection surface is a mixture of three Types.

Figure 9:
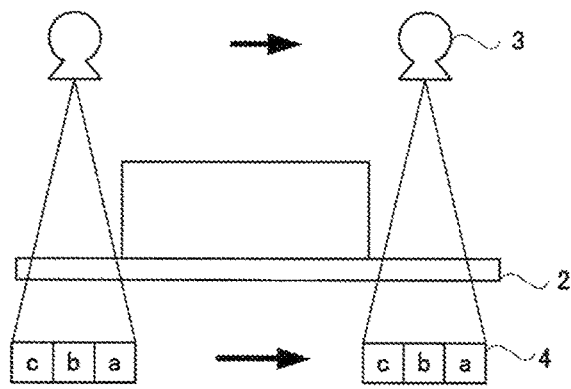
FIG. 9 is a schematic view illustrating the effects of the configuration of Example 1.
Figure 10:
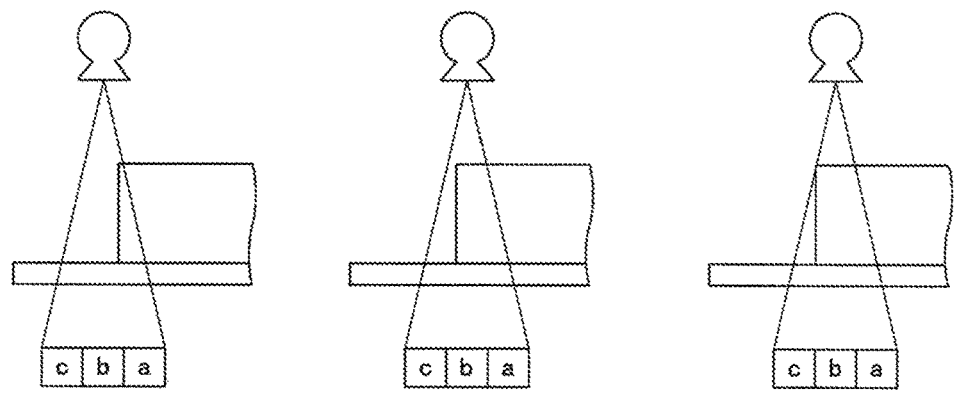
FIG. 10 is a schematic view illustrating the effects of the configuration of Example 1.

FIG. 9 shows how the imaging system 3, 4, and 5 is moving during the imaging. As the imaging system 3, 4, and 5 is moved, the upper stage "a", the middle stage "b", and the lower stage "c" of the detection surface approach the object M in this order and moves away from the object M in this order. FIG. 10 shows the state that the upper stage "a", the middle stage "b", and the lower stage "c" pass through one end portion of the object M. On the left side in FIG. 10, one end portion of the object M is imaged at the upper stage "a" of the detection surface. In the center in FIG. 10, the one end portion of the object M is imaged at the middle stage "b" of the detection surface. On the right side in FIG. 10, the one end portion of the object M is imaged at the lower stage "c" of the detection surface. Thus, the one end portion of the object M is imaged in each of the three stages of the detection surface.

By the way, the self-image shown on the right side in FIG. 7 contains more information on the internal structure of the object M as the dark lines S are closely arranged. The transparent image generation unit 12 acquires the inside state of the object based on how the dark line appearing in the self-image distorts and images it. Therefore, for example, if the number of the dark lines that appeared in the self-image is 4, the transparent image generation unit 12 has no choice but to retrieve the information on the inside of the subject by relying on the small number of dark lines. The transparent image obtained at this time will not become clear.

Figure 11:
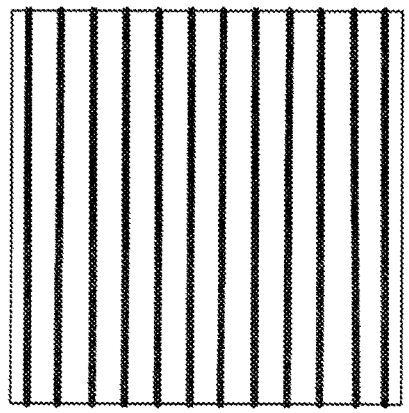
FIG. 11 is a schematic view illustrating the effects of the configuration of Example 1.

In the conventional configuration, if three self-images shown on the right side in FIG. 7 can be separately acquired and these can be synthesized into one self-image as shown in FIG. 11, the density of the dark lines in the self-image is improved to twelve, which is three times. In this case, the transparent image generation unit 12 can refer to a larger number of dark lines, which makes it possible to retrieve the information on the inside of the subject. In this way, a much clearer transparent image can be obtained.

According to the configuration of the present invention, it is possible to obtain the self-image in which the number of dark lines shown in FIG. 11 has been tripled by continuously performing the imaging while moving the imaging system 3, 4, and 5. That is, the self-image generation unit 11 generates a self-image based on the detection data output from the upper stage "a" of the detection surface with reference to the position of the FPD 4 and the position of the imaging system 3, 4, and 5. Similarly, the self-image generation unit 11 generates a self-image based on the detection data output from the middle stage "b" of the detection surface, and generates a self-image based on the detection data output from the lower stage "c" of the detection surface. In this way, the self-image generation unit 11 generates a plurality of self-images different in the dark mark reflection position. At this time, superimposing the three self-images generated by the self-image generation unit 11 results in the image shown in FIG. 11.

How the dark lines actually appear in the FPD 4 according to the present present invention includes intermediate types other than Types 1, 2, and 3 described in FIG. 7. Therefore, the manner that the dark lines appear in the FPD 4 is not limited to three Types, and it also can be thought that there are more types. Based on this idea, it is also possible to configure the self-image generation unit 11 so as to generate self-images of more than the aforementioned three types.

The transparent image generation unit 12 generates a transparent image based on a plurality of self-images generated by the self-image generation unit 11. This transparent image is a much clearer image reflecting the inside of the object. This is because the transparent image was generated based on much more information. In practice, the transparent image generation unit 12 can utilize a conventional configuration in which a self-image in which the dark lines are arranged at the pitch shown in FIG. 11 is converted into a transparent image.

Figure 12:
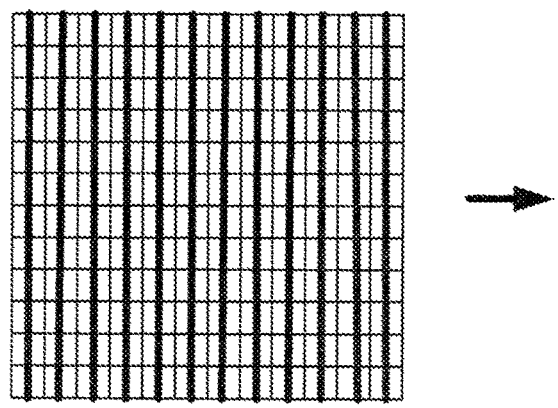
FIG. 12 is a schematic view illustrating the effects of the configuration of Example 1.
Figure 12:
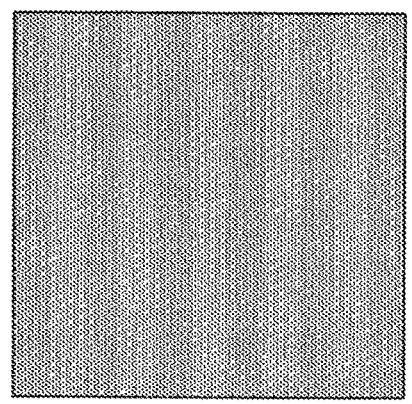

Provided that if the number of the dark lines configuring a self-image is increased, a clearer transparent image can be obtained, there naturally comes a thought that it is better to increase the number of absorption lines 5a in the phase grating 5. The left side in FIG. 12 shows the state in which, according to this idea, the absorption line 5a in the phase grating 5 is increased three times as compared with the case described in FIG. 7. In this case, the dark lines are placed one by one on all detection element rows. Even if it is tried to obtain a self-image in this state, since all the detection elements are the same in condition, only an image having the same pixel value on the entire surface is obtained as shown in the right side in FIG. 12 from the output of the FPD 4, resulting in no self-image. This is because the detection element is too large with respect to the pitch of the absorption line 5a.

In other words, if it is attempted to detect the stripe pattern in which dark lines are arranged at a narrow pitch as shown on the left side in FIG. 12, it is required to further reduce the size of the detection element. There is a limit for the miniaturization of the detection element. However, according to the present invention, it is possible to obtain a self-image as if the absorption line 5a of the phase grating 5 were made three times finer without further reducing the detection element.

The main control unit 21 shown in FIG. 1 is provided for the purpose of comprehensively controlling the respective units 6, 11, 12, and 14. This main control unit 21 is configured by a CPU, and realizes each unit by executing various programs. Further, these units may be divided into and executed by arithmetic units in charge of these units. Each unit can access the storage 27 as necessary. The console 25 is provided for the purpose of inputting an instruction of an operator. Further, the display 26 is provided for the purpose of displaying a transparent image.

As described above, according to the present invention, an imaging device 1 capable of generating a clearer projection image by extracting more information on the inside of the object as compared with a conventional device without miniaturizing the detection element 4a can be provided. That is, according to the configuration of the present invention, the longitudinal direction of the detection surface of the FPD 4 is inclined with respect to the extending direction of the absorption line 5a in the phase grating 5. By configuring the FPD 4 and the phase grating 5 as described above, the self-image of the phase grating 5 appearing as a stripe pattern is reflected on the detection surface in a manner as to be obliquely inclined with respect to the detection surface. This state means that the position (phase) where the stripe pattern of the self-image is reflected differs depending on the position of the detection surface. Therefore, it can be considered that the configuration of Example 1 can realize the same effects as those obtainable when a plurality of self-images having different positions (phases) are obtained.

However, by this alone, the self-image phase for a specific location of the object M is fixed to one. Therefore, according to the configuration of the present invention, imaging is performed while changing the relative position of the imaging system and the object M to perform the imaging of the self-image for different phases at the same place of the object M. By performing such imaging, it is possible to obtain the information on the inside of the object that cannot be obtained unless a phase grating 5 in which absorption lines 5a are arranged at a high density and an FPD 4 in which the detection element 4a is miniaturized are used, without changing the configuration of the FPD 4.

Example 2

Next, a configuration according to Example 2 will be described. The fundamental configuration of Example 2 is the same as that shown in FIG. 1, and therefore the description thereof will be omitted.

Figure 13:
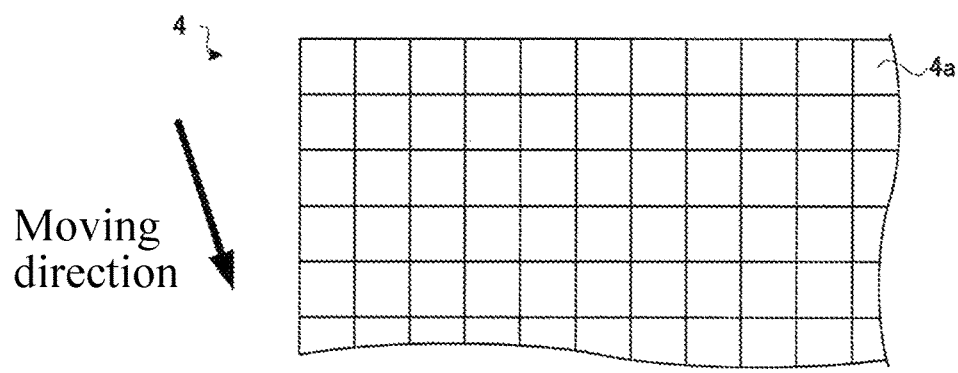
FIG. 13 is a plan view illustrating the configuration of the FPD according to Example 2.

There are four characteristic configurations in Example 2. One of them is the relationship between the moving direction of the imaging system 3, 4, and 5 and the arrangement of the detection elements 4a as shown in FIG. 13. On the detection surface of the FPD 4, detection elements 4a are arranged in a matrix in a plane. The imaging direction of the imaging system 3, 4, and 5 realized by the imaging system moving mechanism 13 is inclined with respect to the longitudinal direction of the detection elements 4a. That is, the moving direction of the imaging system 3, 4, and 5 is a direction along which the imaging system advances by three detection elements of the FPD 4 in the longitudinal direction as the imaging system advances by one detection element of the FPD 4 in the lateral direction.

The second characteristic configuration in Example 2 is the relationship between the moving direction of the imaging system 3, 4, and 5 and the extending direction of the absorption line 5a of the phase grating 5. The phase grating 5 has a plurality of linear absorption lines 5a extending linearly and absorbing an X-ray. The absorption lines 5a are arranged at a predetermined pitch in a direction perpendicular to the extending direction thereof. The imaging direction of the imaging system 3, 4, and 5 realized by the imaging system moving mechanism 13 is inclined with respect to the extending direction of the absorption line 5a.

That is, the longitudinal direction which is the arrangement direction of the detection elements 4a on the detection surface of the FPD 4 coincides with the extending direction of the absorption line 5a of the phase grating 5, and is inclined with respect to the moving direction of the projection of the object M on the detection surface of the FPD 4. In other words, the lateral direction which is the arrangement direction along which the detection elements 4a on the detection surface of the FPD 4 are arranged does not intersect at right angle with the moving direction of the projection of the object M on the detection surface of the FPD 4. More specifically, the moving direction of the imaging system 3, 4, and 5 is a direction in which it advances in the longitudinal direction by an amount corresponding to three detection elements as it advances in the lateral direction by an amount corresponding to one detection element of the FPD 4.

Figure 14:
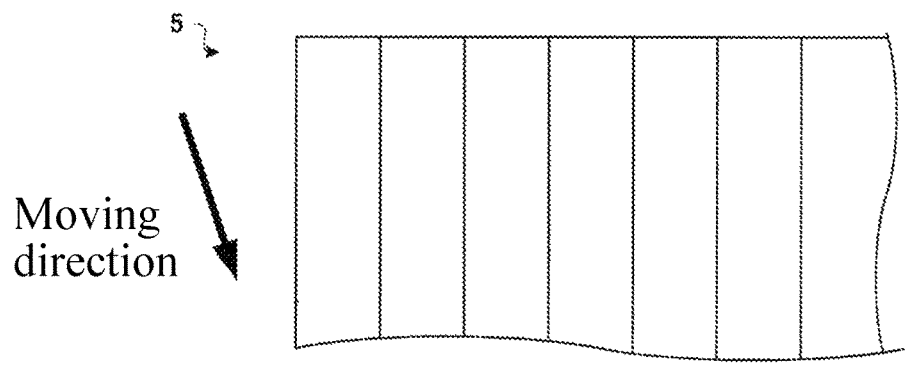
FIG. 14 is a plan view illustrating the configuration of the phase grating according to Example 2.

FIG. 14 illustrates a phase grating 5 of Example 2. The phase grating 5 has a plurality of linear absorption lines 5a extending linearly and absorbing an X-ray. The absorption line 5a is arranged at a predetermined pitch in a direction perpendicular to the extending direction thereof. The absorption line 5a extends in the moving direction of the imaging system 3, 4, and 5, and is parallel to the longitudinal arrangement of the detection elements in the FPD 4. Thus, in other words, the absorption line 5a is inclined with respect to the moving direction of the object M relative to the imaging system. The inclination angle is the same as the angle between the longitudinal direction of the detection surface and the moving direction of the object M relative to the imaging system.

Figure 15:
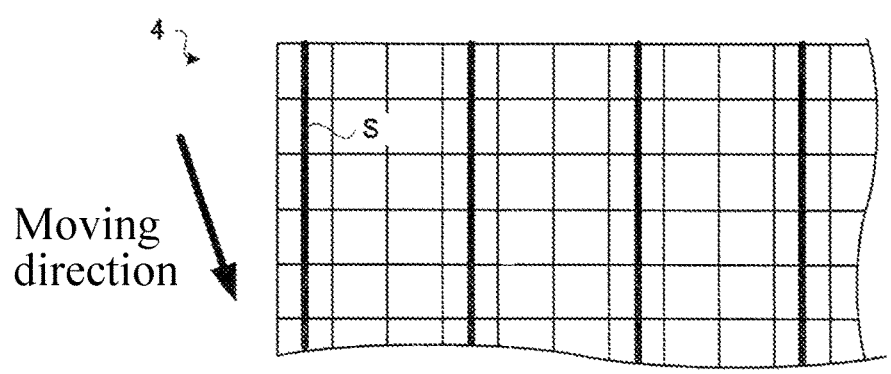
FIG. 15 is a plan view illustrating the configuration of the FPD according to Example 2.

FIG. 15 illustrates a state in which the projection of the phase grating 5 is reflected on the detection surface of the FPD 4. In the FPD 4, a plurality of dark lines S are reflected as a stripe pattern. This dark line S is not the projection itself of the absorption line 5a of the phase grating 5 but the self-image of the phase grating 5 resulting from the Talbot interference. The self-image at this time is, intuitively speaking, formed by overlapping the interference fringes caused by the light interference.

According to FIG. 15, it is understood that the dark line S on the FPD 4 extends along the arrangement of the detection elements 4a. The reason that the extending direction of the dark line S is directed as described above is that the absorption line 5a of the phase grating 5 extends in the longitudinal direction of the FPD 4. Since the extending direction of the dark line S coincides with the extending direction of the absorption line 5a of the phase grating 5, the dark line S extending in the longitudinal direction on the FPD 4 is reflected.

Further, according to FIG. 15, the pitch when the dark line S is arranged in the lateral direction corresponds to three detection elements. This pitch can be arbitrarily changed. Hereinafter, the following description will be made assuming that the dark line S is arranged in the lateral direction at a pitch of three pixels.

The third characteristic configurations in Example 2 is the operation of the self-image generation unit 11. Hereinafter, the operation of the self-image generation unit 11 will be described in detail. For the sake of simplicity, as shown on the left side in FIG. 16, it is assumed that the FPD 4 has detection elements of 3 vertical×3 horizontal. The detection elements are distinguished as D1 to D9, respectively.

Figure 16:
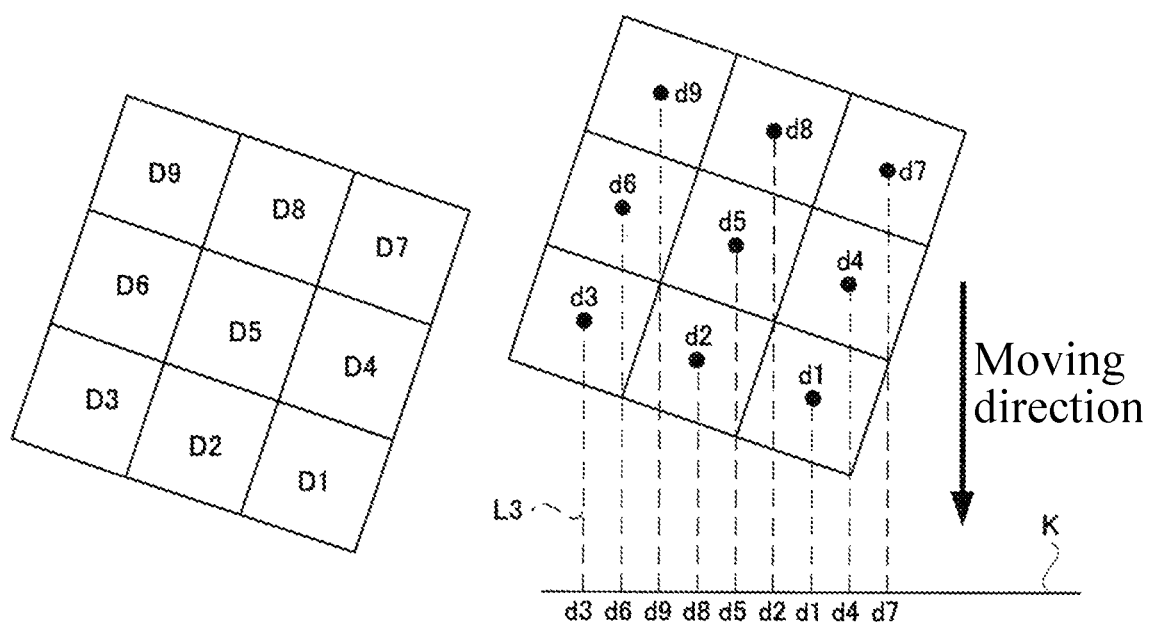
FIG. 16 is a schematic view illustrating the effects of the configuration of Example 2.

The right side in FIG. 16 shows the center points d1 to d9 of the detection elements D1 to D9. The case will be considered in which these center points d1 to d9 are projected on a line segment K perpendicular to the moving direction of the imaging system 3, 4, and 5. Then, the mappings of the center points d1 to d9 are arranged at equal intervals without being overlapped each other. The reason that the mappings are arranged as described above is that the moving direction of the projection of the object M on the detection surface of the FPD 4 coincides with the direction in which it advances in the longitudinal direction by an amount corresponding to three detection elements as it advances in the lateral direction by an amount corresponding to one detection element of the FPD 4. The mappings are arranged on the line segment K at a pitch of $1/10^{1/2}$ times (about 0.32 times) the width of one detection element. Therefore, the distance between adjacent mappings is smaller than the width of one detection element. Hereinafter, the length of $1/10^{1/2}$ times the width of one detection element 1 will be referred to as one unit.

It is assumed that the imaging system 3, 4, and 5 is moved in the moving direction. At this time, the center points d1 to d9 of the detection elements D1 to D9 moves on the individual line segments L1 to L9, respectively. The line segments L1 to L9 extend in the moving direction of the imaging system 3, 4, and 5. Considering that the mappings of the center points d1 to d9 are arranged at equal intervals on the line segment K, the line segments L1 to L9 are arranged at equal intervals (specifically, at intervals of 1 unit) in the lateral direction (the extending direction of the line segment K).

Figure 17:
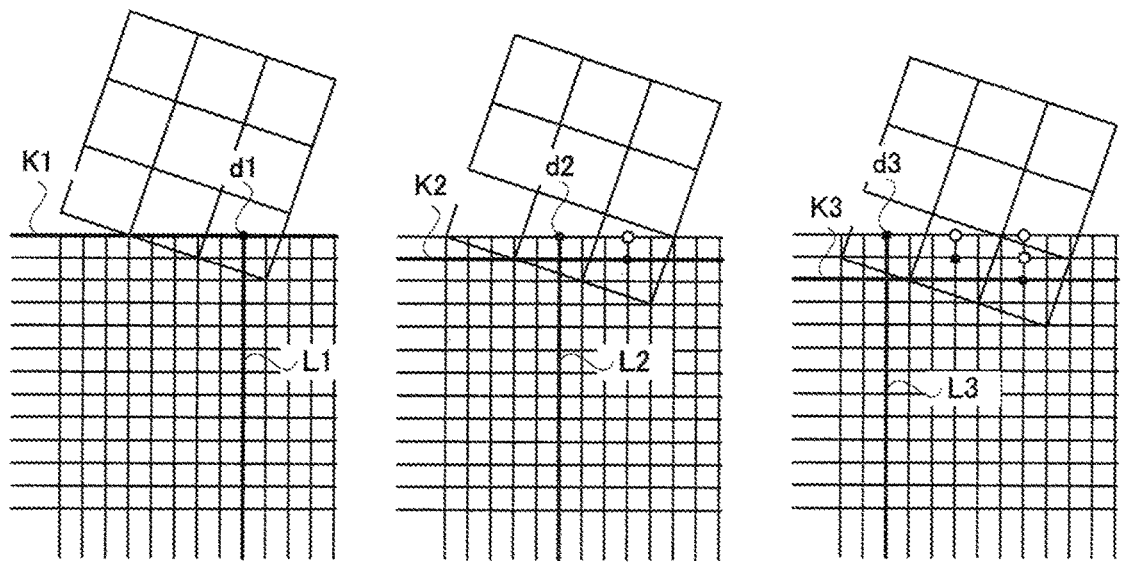
FIG. 17 is a schematic view illustrating the effects of the configuration of Example 2.

The left side in FIG. 17 shows the state when the imaging system 3, 4, and 5 is in the initial position. At this time, the center point d1 of the detection element D1 is, of course, on the line segment L1. The position of the center point d1 at this time is assumed to be on the line segment L1 and the line segment K1 perpendicular to the line segment L1. From this state, it is assumed that the imaging system 3, 4, and 5 is moved in the moving direction one by one unit. The center in FIG. 17 shows the state when the imaging system 3, 4, and 5 is moved by one unit from the initial position. At this time, the center point d1 of the detection element D1 appears at a position moved by one unit from the initial position. The position of the center point d1 at this time is assumed to be on the line segment L1 and the line segment K2 perpendicular to the line segment L1. The right side in FIG. 17 shows the state when the imaging system 3, 4, and 5 is moved by two units from the initial position. At this time, the center point d1 of the detection element D1 appears at a position moved by two units from the initial position. The position of the center point d1 at this time is assumed to be on the line segment L1 and the line segment K3 perpendicular to the line segment L1.

When observing the center in FIG. 17, it is understand that the center point d2 of the detection element D2 is positioned at the intersection of the line segment L2 and the line segment K1. Also, when observing the right side in FIG. 17, it is understand that the center point d2 of the detection element D2 is positioned at the intersection of the line segment L2 and the line segment K2. At the same time, it is understand that the center point d3 of the detection element D3 is positioned at the intersection of the line segment L3 and the line segment K1.

Figure 18:
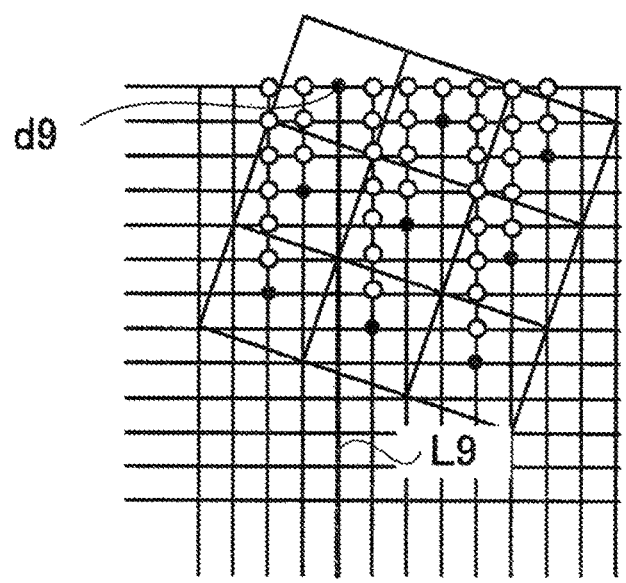
FIG. 18 is a schematic view illustrating the effects of the configuration of Example 2.

In this manner, by moving the imaging system 3, 4, and 5 one by one unit in the moving direction, the center point d1 of the detection element D1 on the line segment L1 moves one by one unit. This situation is the same as in all detection elements. FIG. 18 shows the state when the imaging system 3, 4, and 5 is moved by eight units from the initial position. At this time, it is understand that the center point d9 of the detection element D9 is positioned at the intersection of the line segment L9 and the line segment K1.

The self-image generation unit 11 operates assuming that the detection data detected by each detection element is the detection data at the center point of the detection element. For example, the self-image generation unit 11 assumes that the detection data output by the detection element D1 on the left side in FIG. 17 is the detection result of the X-ray at the intersection of the line segment K1 and the line segment L1. In the same manner, the self-image generation unit 11 assumes that the detection data output by the detection element D1 on the left side in FIG. 17 is the detection result of the X-ray at the intersection of the line segment K2 and the line segment L1 and that the detection data output by the detection element D2 is the detection result of the X-ray at the intersection of the line segment K1 and the line segment L2.

Further, in the same manner, the self-image generation unit 11 assumes that the detection data output by the detection element D1 on the right side in FIG. 17 is the detection result of the X-ray at the intersection of the line segment K3 and the line segment L1 and that the detection data output by the detection element D2 is the detection result of the X-ray at the intersection of the line segment K2 and the line segment L2. And the self-image generation unit 11 assumes that the detection data output by the detection element D3 is the detection result of the X-ray at the intersection of the line segment K1 and the line segment L3.

In FIG. 17 and FIG. 18, the intersection point where the black circle is placed indicates the intersection point at which the detection data is obtained at the current position of the FPD 4, and the intersection point where the white circle is placed indicates the intersection point where the detection data has already been acquired. The intersection points where no circles are placed are unknown intersection points whose detection data is unknown. In the example shown in FIGS. 17 and 18, since there are only nine detection elements, detection data can be obtained only for the nine line segments L1 to 9, but the actual FPD 4 has more detection elements, and therefore there are more line segments from which detection data can be obtained.

As described above, the self-image generation unit 11 samples the detection results of the X-rays on the respective line segments L1 to L9 at one unit intervals based on the detection data repeatedly output from the FPD 4 while the imaging system 3, 4, and 5 is moved one by one unit. As a result, the self-image generation unit 11 can generate an image (self-image) in which the vertical size corresponds to one unit and the horizontal size corresponds to one unit.

The self-image obtained at this time is higher in resolution than the conventional imaging method shown in the upper part in FIG. 7. In the conventional imaging method shown in the upper part in FIG. 7, only the image (self-image) whose longitudinal and lateral sizes each corresponds to the width of one detection element can be obtained. However, the self-image generation unit 11 according to Example 2 can generate an image (self-image) in which the length and width sizes each corresponds to $1/10^{1/2}$ times (about 0.32 times) the width of one detection element. Therefore, according to the method of Example 2, the resolution of the self-image can be increased to $9/8^{1/2}$ times (about 3.2 times) as compared with the conventional method. A clearer transparent image can be obtained when the resolution of the obtained self-image is higher.

The fourth characteristic configuration in Example 2 is that the imaging system 3, 4, and 5 is moved one by one unit in the moving direction as described above. Also in Example 2, the continuous X-ray imaging is realized by the cooperation of the X-ray source control unit 6 and the imaging system moving control unit 14. That is, by the cooperation of both of them, the operation of moving the imaging system 3, 4, and 5 only by one unit and the operation of irradiating the X-ray beam are repeated. The X-ray source control unit 6 makes the X-ray source 3 irradiate the radiation every time the imaging system moving mechanism 13 moves the projection of the object M by $1/10^{1/2}$ time the width of one detection element on the detection surface of the FPD 4.

As described above, the aforementioned configuration shows another embodiment of the present invention. Also with the aforementioned configuration, the imaging device 1 capable of generating a clearer projection image by extracting more information on the inside of the object as compared with a conventional device, without miniaturizing the detection element 4a can be provided. That is, according to the aforementioned configuration, the longitudinal direction of the FPD 4 is inclined with respect to the moving direction of the object M relative to the imaging system. So, when observing the FPD 4 from the moving direction, it looks that the detection elements 4a are arranged at a pitch narrower than the width of one detection element 4a.

In addition to this point of view, the aforementioned configuration repeats the imaging while changing the relative position of the imaging system and the object M to detect the radiation at higher density. By performing such imaging, it is possible to obtain the information on the inside of the object that cannot be obtained unless a phase grating 5 in which the absorption lines 5a are arranged at a high density and an FPD 4 in which the detection element 4a is miniaturized are used, without changing the configuration of the FPD 4.

The present invention is not limited to the aforementioned configuration, and may be modified as follows.

(1) According to the aforementioned Example, the imaging system moving mechanism 13 is configured to move the X-ray source 3 together with the FPD 4 and the phase grating 5, but the present invention is not limited thereto. It may be configured such that the relative position of the object M and the imaging system are changed by configuring the imaging system moving mechanism 13 so as to move the FPD 4 and the phase grating 5 by tracing the locus of a circular arc so as not to change the positional relationship between the X-ray source 3, the FPD 4, and the phase grating 5. Further, the relative position of the object M and the imaging system may be changed by moving the platform 2 without moving the imaging system 3, 4, and 5.

(2) According to the aforementioned configuration, although the object M is placed between the X-ray source 3 and the phase grating 5, the present invention is not limited to the configuration. The platform 2 and the object M may be placed between the phase grating 5 and the FPD 4.

Figure 19:
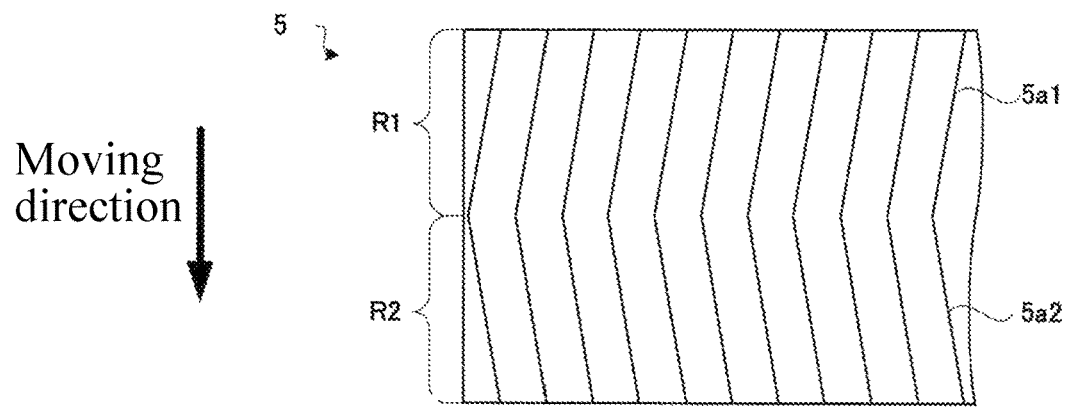
FIG. 19 is a schematic diagram illustrating the configuration of a modified Example of the present invention.

(3) According to the aforementioned Example 1, although the extending direction of the absorption line 5a of the phase grating 5 is inclined in the same direction with respect to the longitudinal direction, the present invention is not limited to this configuration. As shown in FIG. 19, the phase grating 5 may be configured so as to have absorption lines 5a different in the inclination angle with respect to the longitudinal direction of the FPD 4. Such a phase grating 5 has two regions R1 and R2 arranged in the moving direction of the imaging system 3, 4, and 5. The absorption line 5a1 positioned in the region R1 obliquely extends from the upper right to the lower left, and the absorption line 5a2 positioned in the region R2 obliquely extends from the upper left to the lower right. As described above, the phase grating 5 of this modification has the region R1 in which an absorption line 5a absorbing an X-ray and extending in one direction is arranged in a direction perpendicular to the one direction and the region R2 in which an absorption line 5a extending in an intersecting direction which is a direction intersecting with the one direction is arranged in a direction perpendicular to the intersecting direction. The respective regions R1 and R2 are arranged in a direction along which the projection of the object M moves on the detection surface.

Figure 20:
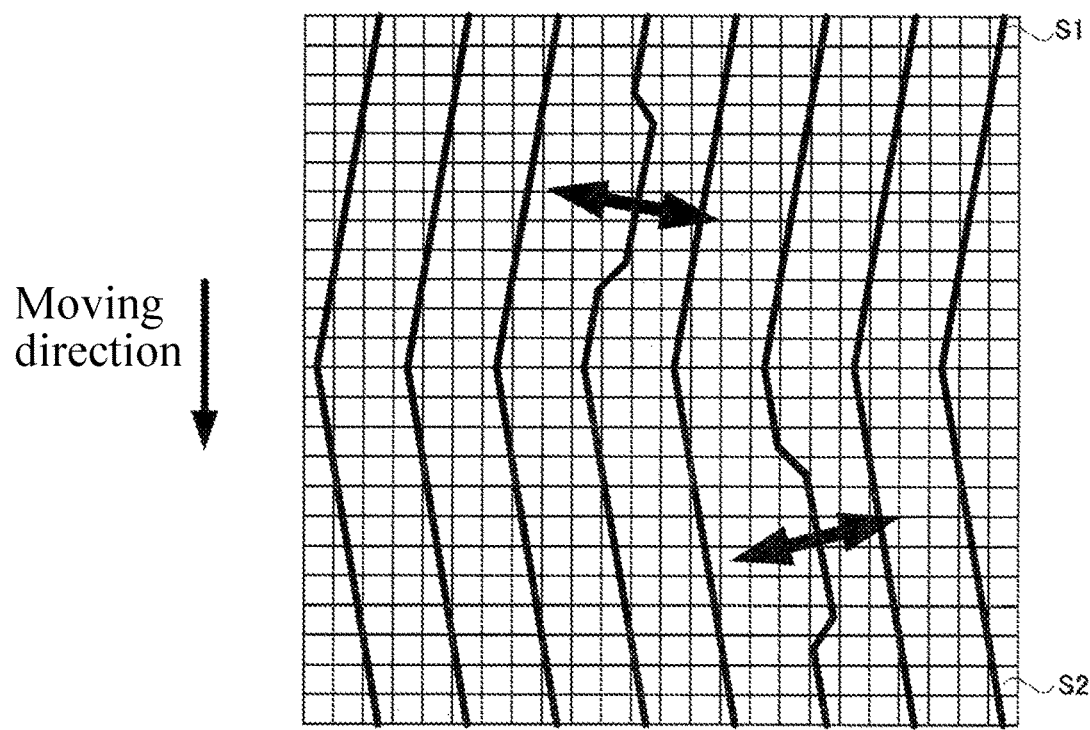
FIG. 20 is a schematic diagram illustrating the configuration of a modified Example of the present invention.

By configuring the phase grating 5 as described above, it is possible to extract more information on the object M when performing the X-ray phase-contrast imaging. FIG. 20 shows the state in which the self-image of the phase grating 5 of the modified example is reflected on the FPD 4. On the upper side of the FPD 4, a stripe pattern in which the dark lines S1 extending diagonally from the upper right to the lower left are arranged in the lateral direction appears. On the lower side of the FPD 4, a stripe pattern in which the dark lines S2 extending diagonally from the upper left to the lower right are arranged in the lateral direction appears. These two stripe patterns configure the self-image of the phase grating 5. That is, the direction perpendicular to the dark line S1 appearing on the upper side of the self-image is a direction from the upper left to the lower right as shown by the arrow in the figure. The direction perpendicular to the dark line S2 appearing on the lower side of the self-image is a direction from the upper right to the lower left as shown by the arrow in the figure.

The imaging device 1 images the internal structure of the object M utilizing the self-image disturbances of the phase grating 5. That is, the dark lines S1 and S2 configuring the self-image in FIG. 20 are distorted in directions perpendicular to the extending directions of the dark lines S1 and S2 due to the transmission of the object M. The imaging device 1 executes the imaging of the internal structure of the object M by observing the distortions. Therefore, when the self-image is generated using the phase grating 5 as described with reference to FIG. 4, the self-image shifts only in a direction perpendicular to the dark line S in FIG. 5 and does not shift in other directions. In the self-image using the phase grating 5, not all information on the internal structure of the object M can be retrieved. By imaging the self-image of the object M again using another phase grating 5 different in the extending direction of the dark line S, new information can be retrieved from the object M.

Figure 21:
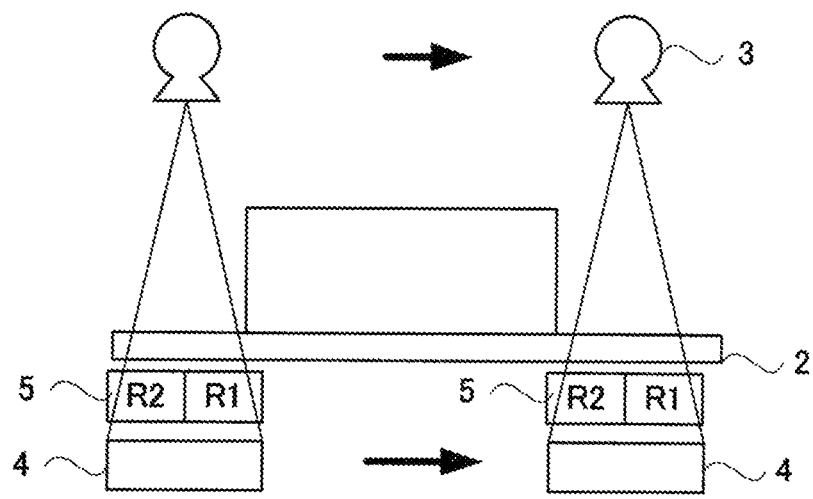
FIG. 21 is a schematic diagram illustrating the configuration of a modified Example of the present invention.
Figure 22:
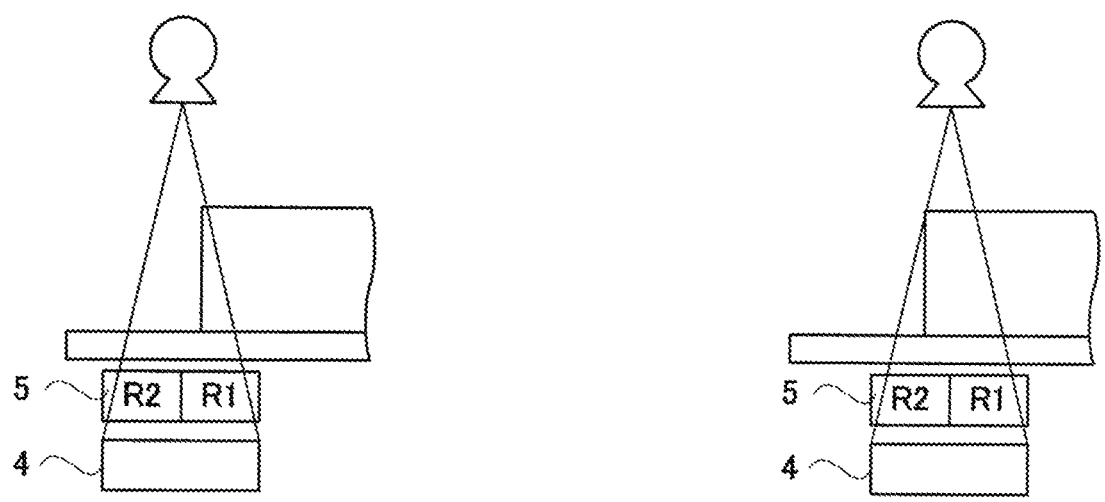
FIG. 22 is a schematic diagram illustrating the configuration of a modified Example of the present invention.

According to the configuration of this modified example, it is possible to image two patterns of self-images different in extending direction of the dark line S by merely performing scan imaging for the subject only once. FIG. 21 illustrates this principle. As the imaging system 3, 4, and 5 moves, the regions R1 and R2 of the phase grating 5 approaches the object M in this order and move away from the object M in this order. FIG. 22 shows the state in which the regions R1 and R2 of the phase grating 5 pass through one end portion of the object M. On the left side in FIG. 22, the X-ray that passed through one end portion of the object M is incident on the region R1 of the phase grating 5. On the right side in FIG. 22, the X-ray that passed through one end portion of the object M is incident on the region R2 of the phase grating 5. In this way, the one end portion of the object M is imaged using two regions of the phase grating 5. That two regions of the phase grating 5 are used at the time of imaging is the same in other portions of the object M.

In this manner, according to this modified example, two patterns of self-images different in extending direction of the dark line S are imaged by merely performing scan imaging for the subject only once. According to this modified example, more information on the internal structure of the object M can be obtained and a transparent image of the object M can be generated.

(4) In the configuration of Example 1, it is configured that the FPD 4 having the detection surface in which the detection elements 4a are arranged in a matrix in a plane is provided and the extending direction of the absorption line 5a of the phase grating 5 is inclined with respect to the arrangement of the detection element 4, but the present invention is not limited to such configuration. Instead of such a configuration, in the present invention, the arrangement direction of the detection elements 4a may be inclined with respect to the absorption line 5a of the phase grating 5.

Figure 23:
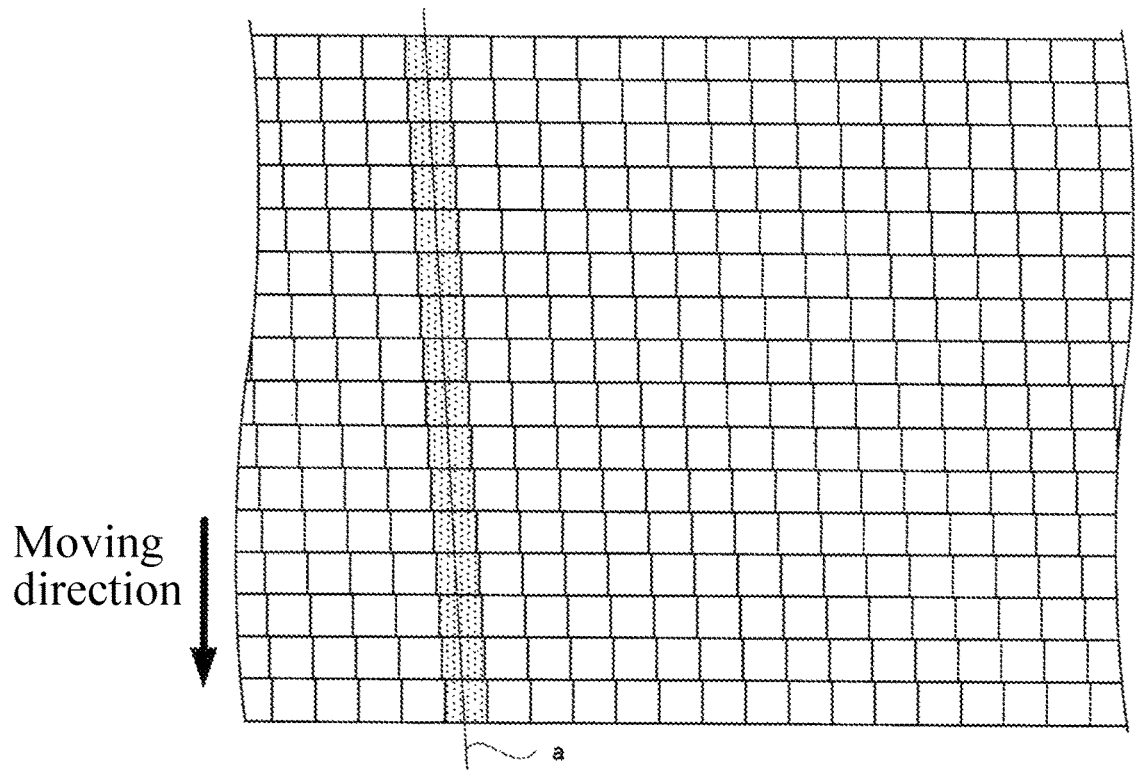
FIG. 23 is a schematic diagram illustrating the configuration of a modified Example of the present invention.

FIG. 23 illustrates the configuration of this modified example. The FPD 4 according to the modified example is configured such that the detection elements 4a are arranged in the inclination direction "a" which is inclined with respect to the moving direction of the imaging system 3, 4, and 5 to constitute an array and that this array is arranged in the lateral direction perpendicular to the moving direction the imaging system 3, 4, and 5 so that the detection elements are arranged two-dimensionally. FIG. 23 illustrates the detection surface on which one of the arrays is represented by shading. In this manner, an array configured by arranging the detection elements 4a on the detection surface of the FPD 4 in the inclination direction "a" which is a direction inclined to the longitudinal direction is arranged in the lateral direction perpendicular to the longitudinal direction two-dimensionally.

Figure 24:
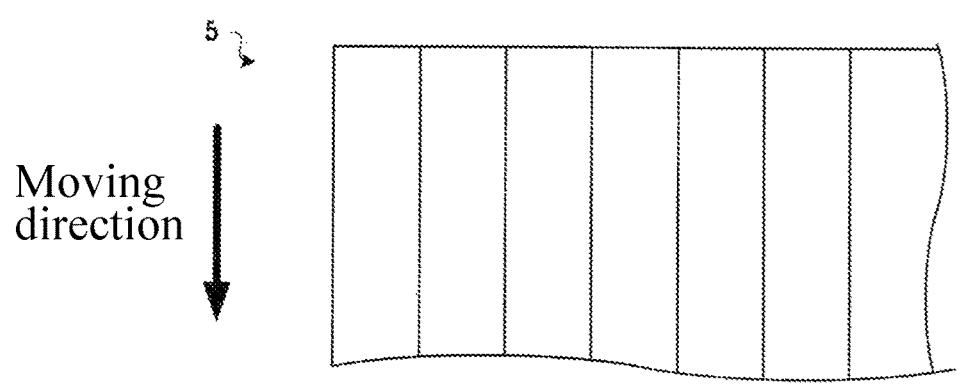
FIG. 24 is a schematic diagram illustrating the configuration of the modified Example of the present invention.

On the other hand, the phase grating 5 in this modified example has absorption lines 5a parallel to the moving direction of the imaging system 3, 4, and 5 as shown in FIG. 24. Therefore, the inclination direction "a" is inclined with respect to the extending direction of the absorption line 5a of the phase grating 5.

Figure 25:
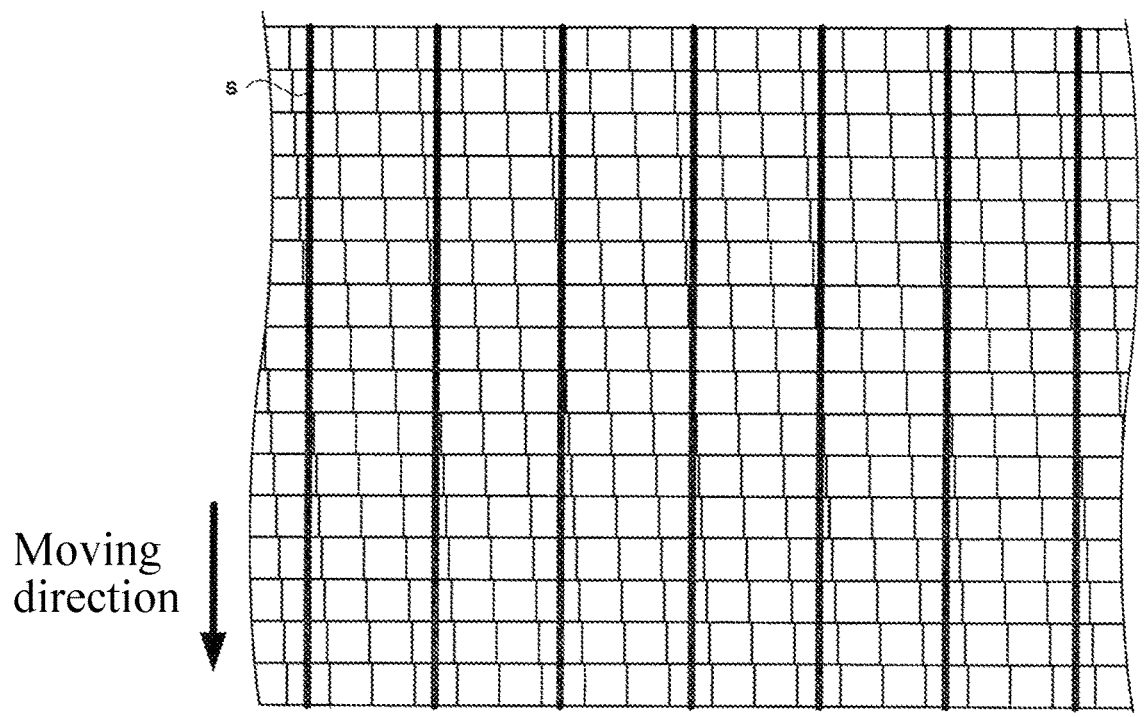
FIG. 25 is a schematic diagram illustrating the configuration of the modified Example of the present invention.
Figure 26:
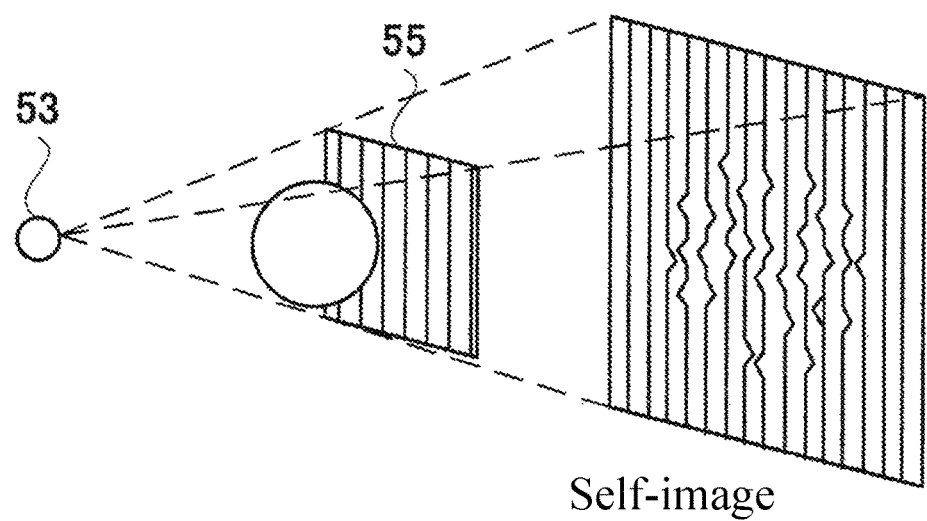
FIG. 26 is a schematic diagram illustrating an apparatus of a conventional configuration.
Figure 27:
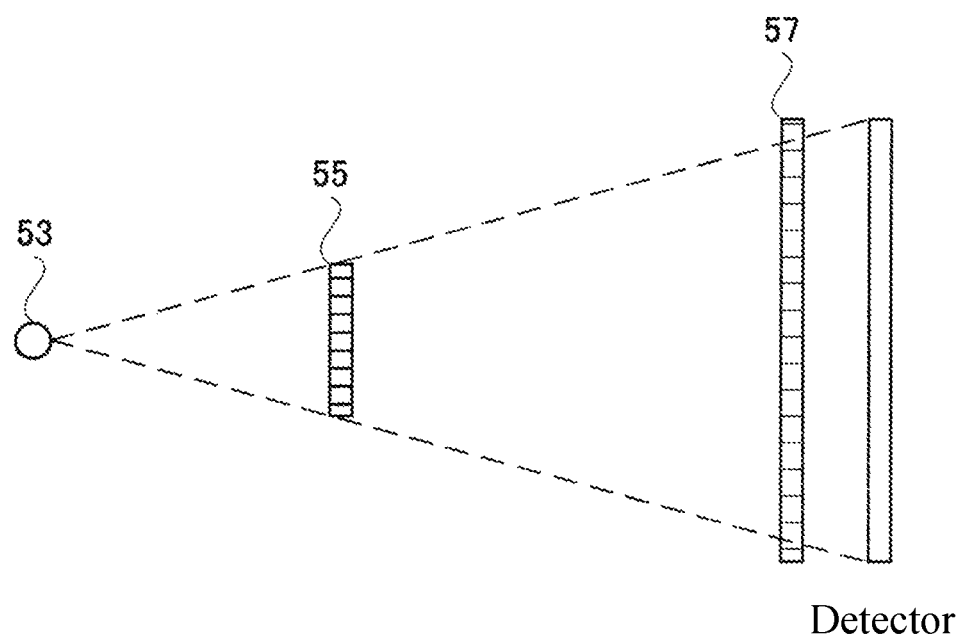
FIG. 27 is a schematic diagram illustrating an apparatus of a conventional configuration.

FIG. 25 shows the state in which the self-image of the phase grating 5 is reflected on the FPD 4 of the modified example. Also with the configuration of this modified example, since the arrangement direction is inclined with respect to the extending direction of the absorption line 5a, the same effects as those obtainable by the configuration of Example 1 can be obtained.

(5) The configuration of the regions R1 and R2 described in FIG. 19 is merely an example of a modified example. As a specific example of the configuration of the regions R1 and R2, as described with reference to FIG. 23, a configuration in which the arrangement of the detection elements of the FPD 4 is inclined with respect to the absorption line 5a can be adopted.

INDUSTRIAL APPLICABILITY

As described above, the present invention is suitably applicable in the industrial field.

DESCRIPTION OF REFERENCE SYMBOLS

3: X-ray source (radiation source)
4a: detection element
4: FPD (detection unit)
5a: absorption line (absorber)

5: phase grating (grating)
6: X-ray source control unit (radiation source controller)
13: imaging system moving mechanism (position changing unit)

The invention claimed is:

1. A radiation phase-contrast imaging device comprising:
an imaging system;
the imaging system being composed of
a radiation source configured to irradiate radiation,
a grating in which an absorber absorbing the radiation and extending in one direction is arranged in a direction perpendicular to the one direction, and
a detection unit configured to detect a self-image of the grating generated by Talbot interference on a detection surface in which a detection element configured to detect the radiation is arranged in a matrix in a plane; and
a position changing unit configured to change a relative position of the imaging system and an object such that a projection of the object moves linearly on the detection surface while keeping s positional relation of the radiation source, the grating, and the detection unit,
wherein a longitudinal direction which is a direction along which the detection element on the detection surface of the detection unit is arranged is inclined with respect to an extending direction of the absorber of the grating, and
wherein the imaging device further comprises a self-image generation unit configured to be operated when imaging is continuously executed while moving the imaging system and generate a plurality of self-images different in a reflecting position of a dark line of the grating based on detection data output from each portion of the detection surface.

2. The radiation phase-contrast imaging device according to claim 1,
wherein a lateral direction which is a direction along which the detection element on the detection surface of the detection unit is arranged is inclined with respect to an arrangement direction of the absorbers of the grating.

3. The radiation phase-contrast imaging device according to claim 1,
wherein the detection surface of the detection unit includes a rectangular region configured such that an array in which a stripe-shaped self-image of one cycle is reflected and the detection element is arranged in one row in the longitudinal direction is arranged in a lateral direction.

4. The radiation phase-contrast imaging device according to claim 1, further comprising a radiation source controller configured to make the radiation source irradiate the radiation every time a projection of the object moves by an amount corresponding to one detection element on the detection surface.

5. The radiation phase-contrast imaging device according to claim 1,
wherein the grating includes a region in which an absorber absorbing the radiation and extending in the one direction is arranged in a direction perpendicular to the one direction, and a region in which an absorber absorbing the radiation and extending in an intersecting direction intersecting with the one direction are arranged in a direction perpendicular to the intersecting direction, and wherein both the regions are arranged in a direction along which the projection of the object moves on the detection surface.

6. A radiation phase-contrast imaging device comprising:
an imaging system;
the imaging system is composed of
a radiation source configured to irradiate radiation,
a grating in which an absorber absorbing the radiation and extending in one direction is arranged in a direction perpendicular to the one direction,
a detection unit configured to detect a self-image of the grating generated by Talbot interference on a detection surface on which a detection element configured to detect the radiation is arranged in a matrix in a plane; and
a position changing unit configured to change a relative position of the imaging system and an object such that a projection of the object moves linearly on the detection surface while keeping a positional relation of the radiation source, the grating, and the detection unit,
wherein a longitudinal direction which is a direction along which the detection element on the detection surface of the detection unit is arranged coincides with an extending direction of the absorber of the grating and is inclined with respect to a moving direction of the projection of the object on the detection surface, and
wherein the imaging device further comprises a self-image generation unit configured to be operated when imaging is continuously executed while moving the imaging system and generate a self-image in which a center point of the detection element is arranged at equal intervals on a line segment perpendicular to a moving direction of the imaging system.

7. The radiation phase-contrast imaging device according to claim 6,
wherein a lateral direction which is a direction along which the detection element on the detection surface of the detection unit is arranged does not perpendicularly intersect with the moving direction of the projection of the object on the detection surface.

8. The radiation phase-contrast imaging device according to claim 6,
wherein on the detection surface of the detection unit, an oblique direction along which it advances by an amount corresponding to one detection element in a lateral direction as it advances from a given detection element in the longitudinal direction by an amount corresponding to three detection elements coincides with the moving direction of the projection of the object on the detection surface.

9. The radiation phase-contrast imaging device according to claim 8, further comprising a radiation source controller configured to make the radiation source execute irradiation of the radiation every time the projection of the object on the detection surface moves by $\frac{1}{10}^{1/2}$ times a width of one detection element.

10. A radiation phase-contrast imaging device comprising:
an imaging system;
the imaging system is composed of
a radiation source configured to irradiate radiation,
a grating in which an absorber absorbing the radiation and extending in one direction is arranged in a direction perpendicular to the one direction, and
a detection unit configured to detect a self-image of the grating generated by Talbot interference on a detection surface for detecting the radiation; and a position changing unit configured to change a relative position of the imaging system and an object such that a projection of the object moves linearly on the detection surface while keeping a positional relation of the radiation source, the grating, and the detection unit, wherein an array configured by detection elements arranged in a inclined direction which is a direction inclined with respect to a longitudinal direction is two-dimensionally arranged by being arranged in a lateral direction perpendicular to the longitudinal direction on the detection surface of the detection unit, and wherein the inclined direction is inclined with respect to an extending direction of the absorber of the grating, and wherein the imaging device further comprises a self-image generation unit configured to be operated when imaging is continuously executed while moving the imaging system and generate a plurality of self-images different in a reflecting position of a dark line of the grating based on detection data output from each portion of the detection surface.

* * * * *